United States Patent [19]

Jaetsch et al.

[11] Patent Number: 5,508,278
[45] Date of Patent: Apr. 16, 1996

[54] PYRIDO[1,2,3-D,E] [1,3,4]BENZOXADIAZINE DERIVATIVES

[75] Inventors: Thomas Jaetsch, Köln; Burkhard Mielke; Uwe Petersen, both of Leverkusen; Thomas Philipps, Köln; Thomas Schenke, Bergisch Gladbach; Klaus D. Bremm, Wuppertal; Rainer Endermann, Wuppertal; Karl G. Metzger, Wuppertal; Martin Scheer, Wuppertal; Michael Stegemann; Heinz-Georg Wetzstein, both of Leverkusen, all of Germany

[73] Assignee: Bayer Aktiengesellschaft, Leverkusen, Germany

[21] Appl. No.: 296,944

[22] Filed: Aug. 26, 1994

[30] Foreign Application Priority Data

Sep. 2, 1993 [DE] Germany .................. 43 29 600.9

[51] Int. Cl.$^6$ ................ C07D 273/04; A01N 43/88; A61K 31/535
[52] U.S. Cl. ................ 514/229.2; 514/185; 544/64; 544/66
[58] Field of Search ........... 544/64, 66; 514/185, 514/229.2

[56] References Cited

U.S. PATENT DOCUMENTS

| | | | |
|---|---|---|---|
| 4,801,584 | 1/1989 | Yokose et al. | 514/183 |
| 4,988,709 | 1/1991 | Ogata et al. | 514/314 |
| 4,990,517 | 2/1991 | Petersen et al. | 514/300 |
| 5,202,337 | 4/1993 | Petersen et al. | 514/312 |

FOREIGN PATENT DOCUMENTS

| | | |
|---|---|---|
| 0259804 | 3/1988 | European Pat. Off. . |
| 0287951 | 10/1988 | European Pat. Off. . |
| 0343524 | 11/1989 | European Pat. Off. . |
| 0391132 | 10/1990 | European Pat. Off. . |
| 0550903 | 7/1993 | European Pat. Off. . |
| 0572259 | 12/1993 | European Pat. Off. . |
| WO9212146 | 7/1992 | WIPO . |
| WO9417074 | 8/1994 | WIPO . |

OTHER PUBLICATIONS

Eur J. Med. Chem., 1991, vol. 26, pp. 889–906; "Synthesis and antibacterial activity of new 7–(aminoazabicycloalkkanyl) . . . ", M. Ogata et al.
Petersen et al, Chemical Abstract 118: 233894q, abstract of DE 4,120,646 (1993).
Nakagawa et al Chemical Abstract 116: 21064c, abstract of JP 03–188,080 (1992).
Ogata, et al., Eur. J. Med Chem, 26 809–906 (1991).

*Primary Examiner*—John M. Ford
*Attorney, Agent, or Firm*—Sprung Horn Kramer & Woods

[57] ABSTRACT

Novel bactericidal pyrido[1,2,3-d,e,][1,3,4]benzoxadiazine derivatives of the formula (I)

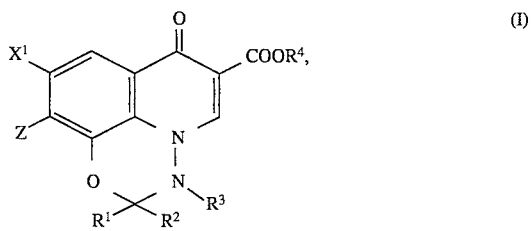

in which $R^1$ is hydrogen or $C_1$–$C_4$-alkyl optionally substituted by hydroxyl or halogen, $R^2$ independently of $R^1$ is hydrogen or methyl, $R^3$ is hydrogen or $C_1$–$C_4$-alkyl, $R^4$ is hydrogen, $C_1$–$C_4$-alkyl optionally substituted by hydroxyl, methoxy, amino, methylamino or dimethylamino, or (5-methyl-2-oxo-1,3-dioxol-4-yl)-methyl, $X^1$ is hydrogen or halogen and Z is a radical of the structure

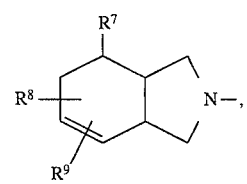

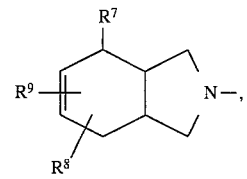

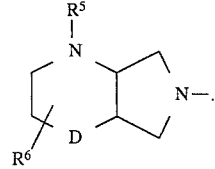

9 Claims, No Drawings

PYRIDO[1,2,3-D,E][1,3,4] BENZOXADIAZINE DERIVATIVES

The invention relates to novel pyrido[1,2,3-d,e][1,3,4]-benzoxadiazine derivatives, to processes for their preparation and to antibacterial compositions and feed additives in which they are present.

It has already been disclosed that such pyridobenzoxadiazinecarboxylic acids have antibacterial activity. Examples of this can be found in EP-O 259 804, EP-O 343 524 and European Journal of Medicinal Chemistry 26, 889 (1991).

Compounds of the general formula (I)

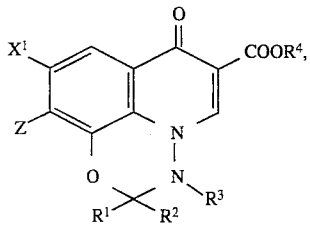

have now been found in which $R^1$ is hydrogen or $C_1$–$C_4$-alkyl optionally substituted by hydroxyl or halogen, $R^2$ independently of $R^1$ is hydrogen or methyl, $R^3$ is hydrogen or $C_1$–$C_4$-alkyl, $R^4$ is hydrogen, $C_1$–$C_4$-alkyl optionally substituted by hydroxyl, methoxy, amino, methylamino or dimethylamino, or (5-methyl-2-oxo-1,3-dioxol-4-yl)methyl, $X^1$ is hydrogen or halogen and Z is a radical of the structure

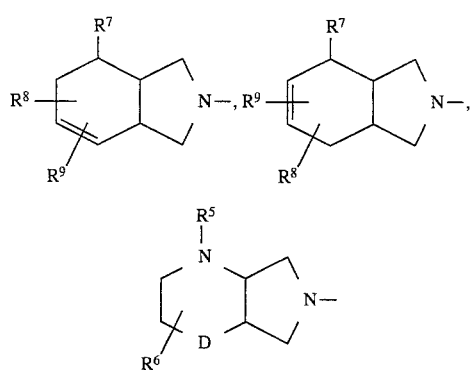

in which $R^7$ is hydrogen, hydroxyl, —$NR^{10}R^{11}$, hydroxymethyl, —$CH_2$—$NR^{10}R^{11}$, carboxyl methoxycarbonyl or ethoxycarbonyl
  $R^{10}$ being hydrogen, $C_1$–$C_3$-alkyl optionally substituted by hydroxyl, alkoxycarbonyl having 1 to 4 C atoms in the alkoxy moiety, or $C_1$–$C_3$-acyl, and
  $R^{11}$ being hydrogen or methyl, $R^8$ is hydrogen, linear or branched $C_1$–$C_3$-alkyl or cyclopropyl, $R^9$ is hydrogen or methyl, $R^6$ is hydrogen or methyl, $R^5$ is hydrogen, methyl or a radical of the structure —CH=CH—$CO_2R^{5'}$, —$CH_2$—$CH_2$—$CO_2R^{5'}$, —$CH_2$—CO—$CH_3$ or —$CH_2$—$CH_2$—CN, $R^{5'}$ being methyl or ethyl, and B is —$CH_2$—, O or a direct bond.

The compounds of the formula (I) can be present in the form of racemates or as enantiomerically pure compounds, in the form of their pharmaceutically acceptable hydrates and acid addition salts or in the form of their alkali metal, alkaline earth metal, silver and guanidinium salts.

The compounds of the formula (I) are obtained by reacting compounds of the formula (II)

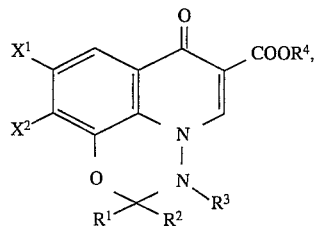

in which $R^1$, $R^2$, $R^3$, $R^4$ and $X^1$ are as defined above and $X^2$ is halogen, especially fluorine or chlorine, with compounds of the formula (III)

$$Z-H \qquad (III),$$

in which

Z is as defined above, optionally in the presence of acid acceptors.

Compared with known representatives of this structural type, the compounds according to the invention have a more potent antibacterial action, especially in the Gram-positive range. They are therefore suitable as active ingredients for human and veterinary medicine, the latter also including the treatment of fish for the therapy or prophylaxis of bacterial infections.

Preferred compounds of the formula (I) are those in which $R^1$ is hydrogen or $C_1$–$C_3$-alkyl optionally substituted by hydroxyl, $R^2$ independently of $R^1$ is hydrogen or methyl, $R^3$ is hydrogen, methyl or ethyl, $R^4$ is hydrogen, $C_1$–$C_4$-alkyl optionally substituted by hydroxyl, methoxy, amino, methylamino or dimethylamino, or (5-methyl-2-oxo-1,3-dioxol-4-yl)methyl, $X^1$ is hydrogen, fluorine or chlorine and Z is a radical of the structure

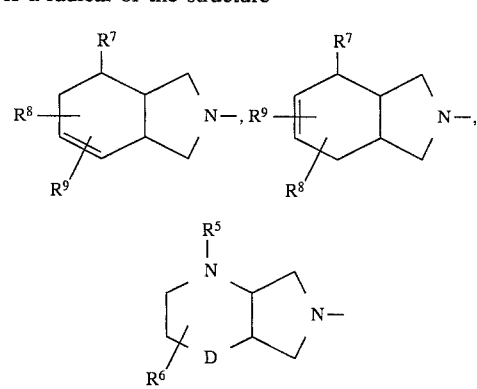

in which $R^7$ hydrogen, hydroxyl, —$NR^{10}R^{11}$, hydroxymethyl or —$CH_2$—$NR^{10}R^{11}$,
  $R^{10}$ being hydrogen, $C_1$–$C_2$-alkyl optionally substituted by hydroxyl, alkoxycarbonyl having 1 to 4 C atoms in the alkoxy moiety, or $C_1$–$C_3$-acyl, and
  $R^{11}$ being hydrogen or methyl, $R^8$ is hydrogen, linear or branched $C_1-C_3$-alkyl or cyclopropyl, $R^9$ is hydrogen or methyl, $R^5$ is hydrogen or methyl, $R^6$ is hydrogen and B is —$CH_2$—, O or a direct bond, their pharmaceutically acceptable hydrates and acid addition salts and their alkali metal, alkaline earth metal, silver and guanidinium salts.

Particularly preferred compounds of the formula (I) are those in which $R^1$ is hydrogen or methyl, $R^2$ is hydrogen, $R^3$ is methyl or ethyl, $R^4$ is hydrogen, methyl or ethyl, $X^1$ is fluorine and Z is a radical of the structure

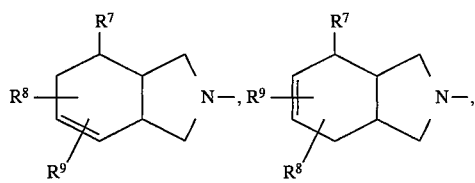

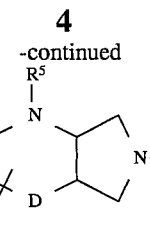

in which $R^7$ is hydrogen, hydroxyl, —$NR^{10}R^{11}$, hydroxymethyl or —$CH_2$—$NR^{10}R^{11}$, $R^{10}$ being hydrogen, methyl, alkoxycarbonyl having 1 to 4 C atoms in the alkoxy moiety, or $C_1-C_3$-acyl, and $R^{11}$ being hydrogen or methyl, $R^8$ is hydrogen, linear or branched $C_1-C_3$-alkyl or cyclopropyl, $R^6$ is hydrogen, $R^9$ is hydrogen or methyl, $R^5$ is hydrogen or methyl and D is —$CH_2$—, O or a direct bond, their pharmaceutically acceptable hydrates and acid addition salts and their alkali metal, alkaline earth metal, silver and guanidinium salts.

The following compounds of the formula (I) may be specifically mentioned:

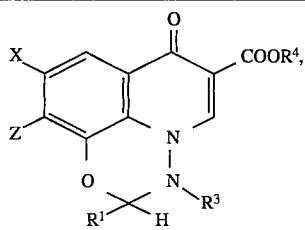

| $R^1$ | $R^3$ | $R^4$ | Z | X |
|---|---|---|---|---|
| H | Me | H | (CH₃-N, bicyclic piperidine-pyrrolidine) | F |
| H | Me | H | (CH₃-N, bicyclic morpholine-pyrrolidine with O) | F |
| H | Me | H | (CH₃-N, bicyclic pyrrolidine-pyrrolidine) | F |
| H | Me | Et | (H-N, bicyclic piperidine-pyrrolidine) | F |

-continued
| | | | | |
|---|---|---|---|---|
| H | Et | H | 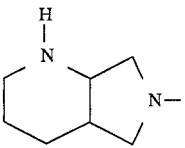 | F |
| Me | Me | H | 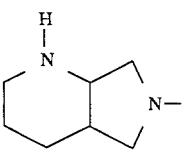 | F |
| Me | Me | H | 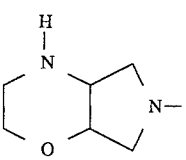 | F |
| CH$_2$OH | Me | H | 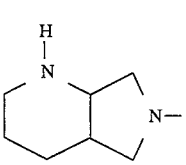 | F |
| H | H | H | 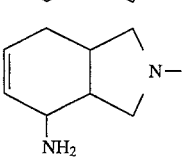 | F |
| H | H | —CH$_2$—CH$_2$—OCH$_3$ | 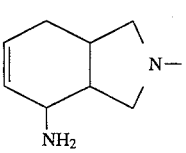 | F |
| CH$_3$ | H | H | 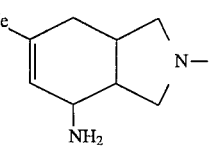 | F |
| CH$_3$ | CH$_3$ | H | 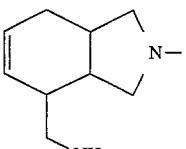 | F |
| H | CH$_3$ | Ethyl | 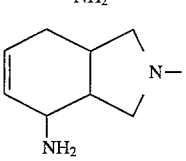 | F |
| H | CH$_3$ | —CH$_2$—CH$_2$—NH$_2$ | 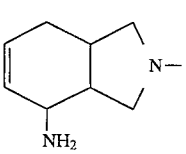 | F |
| H | CH$_3$ | —CH$_2$—CH$_2$—OCH$_3$ | 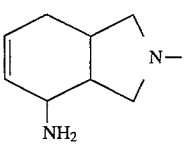 | F |

-continued
| | | | | |
|---|---|---|---|---|
| H | H | Ethyl | 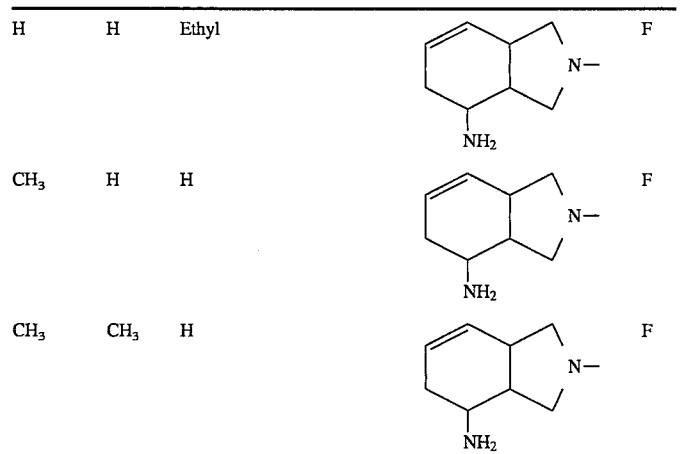 | F |
| CH₃ | H | H | | F |
| CH₃ | CH₃ | H | | F |
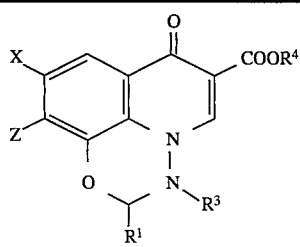
| R¹ | R³ | R⁴ | Z | X |
|---|---|---|---|---|
| H | Me | H | 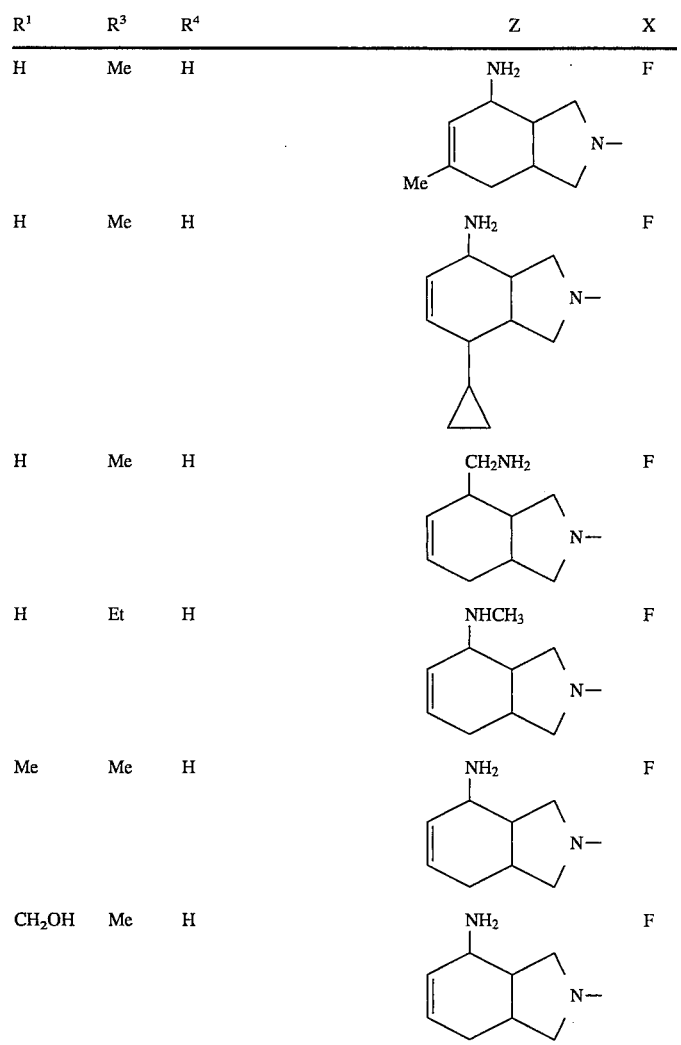 | F |
| H | Me | H | | F |
| H | Me | H | | F |
| H | Et | H | | F |
| Me | Me | H | | F |
| CH₂OH | Me | H | | F |

-continued

| | | | | | |
|---|---|---|---|---|---|
| H | Me | H | NH₂ (on bicyclic structure) | | F |
| H | Me | H | NHCH₃ (on bicyclic structure) | | F |
| H | Me | H | NHC₂H₅ (on bicyclic structure) | | F |
| H | Me | H | N(CH₃)₂ (on bicyclic structure) | | F |
| H | Me | H | CH₂NH₂ (on bicyclic structure) | | F |
| H | Me | H | CH₂NHCH₃ (on bicyclic structure) | | F |
| H | Me | H | NH₂, H₃C (on bicyclic structure) | | F |
| H | Me | H | NH₂, CH₃ (on bicyclic structure) | | F |
| H | Me | H | NH₂, CH₃ (on bicyclic structure) | | F |
| H | Me | H | NHCO₂Et (on bicyclic structure) | | F |
| H | Me | H | (bicyclic structure, no substituent) | | F |

-continued
| | | | | |
|---|---|---|---|---|
| H | Me | H | CH₂OH 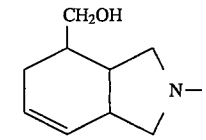 | F |
| H | Me | H | CH₂NHCO₂Et 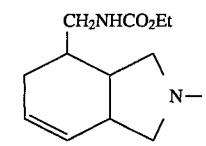 | F |
| Me | Me | H | NHCH₃ 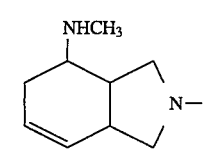 | F |
| Me | Me | H | CH₂NH₂ 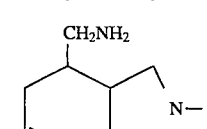 | F |
| CH₂OH | Me | H | NH₂ 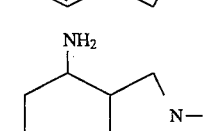 | F |
| CH₂OH | Me | H | NHCH₃ 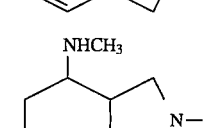 | F |
| CH₂OH | Me | H | CH₂NH₂ 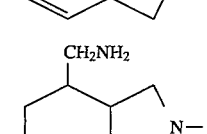 | F |
| H | Et | H | NH₂ 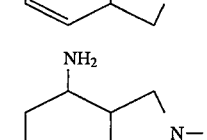 | F |
| H | Et | H | NHCH₃ 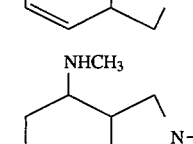 | F |
| H | Me | Et | NH₂ 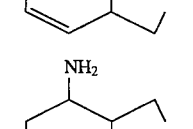 | F |
| H | Me | Et | NHCH₃ 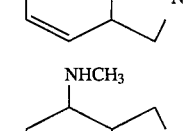 | F |

If compounds of the formula (I) are prepared for example using 9,10-difluoro-3-methyl-7-oxo-2,3-dihydro-7H-pyrido[1,2,3-d,e][1,3,4]benzoxadiazine-6-carboxylic acid and 2,8-diazabicyclo[4.3.0]nonane, the course of the reaction can be represented by the following equation:

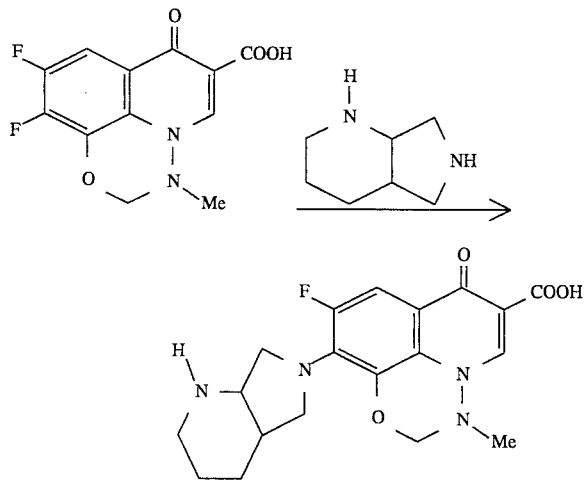

The compounds of the formula (I) used as starting compounds are known or can be prepared by known processes. They can optionally be used as racemates, enantiomers or pure diastereoisomers.

Examples which may be mentioned are:
9,10-difluoro-3-methyl-7-oxo-2,3-dihydro-7H -pyrido[1,2,3-d,e][1,3,4]benzoxadiazine-6-carboxylic acid
9,10-difluoro-2,3-dimethyl-7-oxo-2,3-dihydro-7H-pyrido[1,2,3-d,e][1,3,4]benzoxadiazine-6-carboxylic acid
9,10-difluoro-2-(hydroxymethyl)-3-methyl-7-oxo-2,3-dihydro-7H-pyrido[1,2,3-d,e][1,3,4]benzoxadiazine-6-carboxylic acid
9,10-difluoro-3-ethyl-7-oxo-2,3-dihydro-7H-pyrido[1,2,3-d,e][1,3,4]benzoxadiazine-6-carboxylic acid
ethyl 9,10-difluoro-3-methyl-7-oxo-2,3-dihydro-7H-pyrido[1,2,3-d,e][1,3,4]benzoxadiazine-6-carboxylate The amines of the formula (III) used as starting compounds are known. Chiral amines can be used either as racemates or else as enantiomerically or diastereoisomerically pure compounds.

Examples which may be mentioned are:
2,7-diazabicyclo[3.3.0]octane
2-methyl-2,7-diazabicyclo[3.3.0]octane
2,8 -diazabicyclo[4.3.0]nonane
2-methyl-2,8-diazabicyclo[4.3.0]nonane
2-oxa-5,8-diazabicyclo[4.3.0]nonane
5-methyl-2-oxa-5,8-diazabicyclo[4.3.0]nonane
2-amino-8-azabicyclo[4.3.0]non-3-ene
2-methylamino-8-azabicyclo[4.3.0]non-3-ene
4-methyl-2-methylamino-8-azabicyclo[4.3.0]non-3-ene
5-methyl-2-methylamino-8-azabicyclo[4.3.0]non-3-ene
2-dimethylamino-8-azabicyclo[4.3.0]non-3-ene
2-ethylamino-8-azabicyclo[4.3.0]non-3-ene
2-methylaminomethyl-8-azabicyclo[4.3.0]non-3-ene
2-hydroxy-8-azabicyclo[4.3.0]non-3-ene
5-isopropyl-2-methylamino-8-azabicyclo[4.3.0]non-3-ene
2-amino-5-isopropyl-8-azabicyclo[4.3.0]non-3-ene
2-amino-5-methyl-8-azabicyclo[4.3.0]non-3-ene
2-hydroxymethyl-8-azabicyclo[4.3.0]non-3-ene
2-amino-5-cyclopropyl-8-azabicyclo[4.3.0]non-3-ene
8-azabicyclo[4.3.0]non-2-ene
ethyl 8-azabicyclo[4.3.0]non-4-ene-2-carboxylate
2-hydroxymethyl-8-azabicyclo[4.3.0]non-4-ene
2-amino-8-azabicyclo[4.3.0]non-4-ene
2-ethoxycarbonylamino-8-azabicyclo[4.3.0]non-4-ene
2-tert-butoxycarbonylamino-8-azabicyclo[4.3.0]non-4-ene
2-benzyloxycarbonylamino-8-azabicyclo[4.3.0]non-4-ene
2-allyloxycarbonylaminomethyl-8-azabicyclo[4.3.0]non-4-ene
2-aminomethyl-8-azabicyclo[4.3.0]non-4-ene
2-ethoxycarbonylaminomethyl-8-azabicyclo[4.3.0]non-4-ene
2-tert-butoxycarbonylaminomethyl-8-azabicyclo[4.3.0]non-4-ene
2-methylamino-8-azabicyclo[4.3.0]non-4-ene
2-ethylamino-8-azabicyclo[4.3.0]non-4-ene
2-cyclopropylamino-8-azabicyclo[4.3.0]non-4-ene
2-dimethylamino-8-azabicyclo[4.3.0]non-4-ene
2-[(2-hydroxyethyl)-amino]-8-azabicyclo[4.3.0]non-4-ene
2-amino-1-methyl-8-azabicyclo[4.3.0]non-4-ene
2-amino-2-methyl-8-azabicyclo[4.3.0]non-4-ene
2-amino-3-methyl-8-azabicyclo[4.3.0]non-4-ene
2-ethoxycarbonylamino-3-methyl-8-azabicyclo[4.3.0]non-4-ene
2-tert-butoxycarbonylamino-3-methyl-8-azabicyclo[4.3.0]non-4-ene
2-benzyloxycarbonylamino-3-methyl-8-azabicyclo[4.3.0]non-4-ene
2-allyloxycarbonylaminomethyl-3-methyl-8-azabicyclo[4.3.0]non-4-ene
2-amino-4-methyl-8-azabicyclo[4.3.0]non-4-ene
2-amino-5-methyl-8-azabicyclo[4.3.0]non-4-ene
2-amino-6-methyl-8-azabicyclo[4.3.0]non-4-ene
2-amino-7-methyl-8-azabicyclo[4.3.0]non-4-ene
2-amino-9-methyl-8-azabicyclo[4.3.0]non-4-ene The substituted 8-azabicyclo[4.3.0]non-4-enes and 8-azabicyclo[4.3.0]non-2-ene form the subject of a patent application by the Applicant (Le A 29 200) which does not yet belong to the state of the art.

Compounds of the general formula (IV)

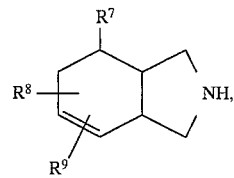

in which $R^7$, $R^8$ and $R^9$ are as defined above, are obtained by reacting suitable dienes with suitable dienophiles in a Diels-Alder reaction, which can be carried out intermolecularly or intramolecularly, and then optionally carrying out further chemical reactions to construct the pyrrolidine ring, if appropriate, and to introduce substituents desired for the biological action, and, as the last step, cleaving the protecting group from the pyrrolidine nitrogen.

If the Diels-Alder reaction is carried out intramolecularly, compounds of the formula (1) or (2)

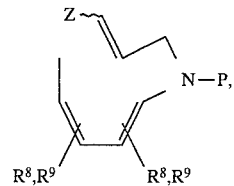

-continued

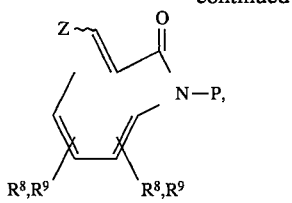

in which

R[8] and R[9] are as defined above,

P is a protecting group (for example allyl, acyl, carbamoyl or trityl) and

Z is hydrogen, a carboxyl, carboxylic acid ester or carboxamide group, CN or $NO_2$, are converted to compounds of the formula (3) [starting from (1)] or (4) [starting from (2)]

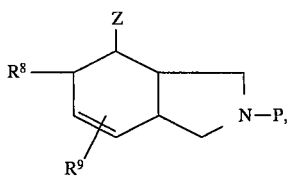

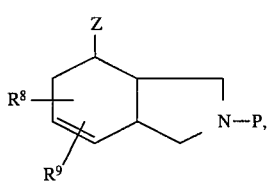

in which

R[8], R[9], P and Z are as defined above.

Some intramolecular Diels-Alder reactions of a similar type are known: J. M. Mellor, A. M. Wagland; J. Chem. Soc. Perkin I, 997–1005 (1989); W. R. Roush, S. E. Hall; J. Am. Chem. Soc. 103, 5200 (1980); E. Ciganek; Organic Reactions 32, 1–374 (1984). However, these studies give no indication of protecting groups which are suitable for the reaction and at the same time can subsequently be cleaved without difficulty.

If the Diels-Alder reaction is carried out intermolecularly, dienes of the formula (5) are reacted with dienophiles of the formula (6) to give compounds of the formula (7) and, optionally after modification of the groups $Z^1$ and $Z^2$, for example conversion of a cyclic carboxylic anhydride to a diester, are cyclized to the lactams of the formula (8) with cleavage of the protecting groups $P_1$ or $P^1$ and $P^2$.

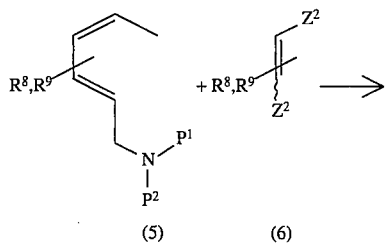

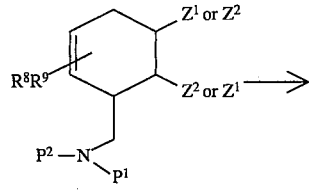

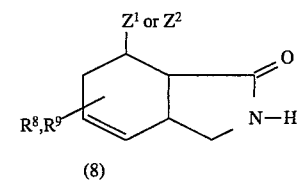

In the formulae (5), (6), (7) and (8), R[8] and R[9] are as defined above, $P^1$ is an acyl or carbamoyl protecting group if $P^2$ is hydrogen, or $P^1$ forms an imide together with $P^2$, and $Z^1$ and $Z^2$ are hydrogen, carboxyl, carboxylic acid ester or carboxamide groups, CN or $NO_2$, it being necessary for at least one of the two groups $Z^1$ or $Z^2$ to be a carboxylic acid ester group, a carboxamide group or CN, or $Z^1$ and $Z^2$ together form a bridge to give a cyclic carboxylic anhydride.

Preferred protecting groups P, $P^1$ and $P^2$ are those with which, under the conditions used to cleave them, the cyclisation to the lactam takes place and, if appropriate, a second, still free carboxyl group is esterified with the alcohol used as the solvent, so that all the reaction steps can be carried out in a one-pot reaction, and possibly diastereoisomerically and enantiomerically pure starting materials are not converted in uncontrolled manner to mixtures of isomers which cannot be resolved or cannot easily be resolved.

Examples which may be mentioned are:

1. the tert-butoxycarbonyl protecting group (cleavage with aqueous or alcoholic acids)
2. the phthalimido protecting group (aminolysis with primary amines in aqueous or anhydrous alcohols as solvent)

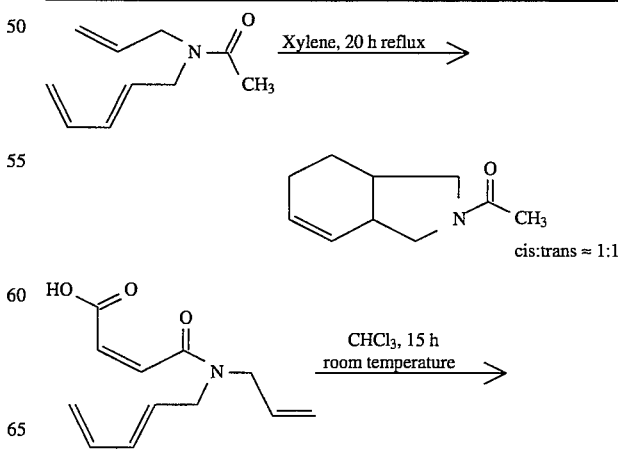

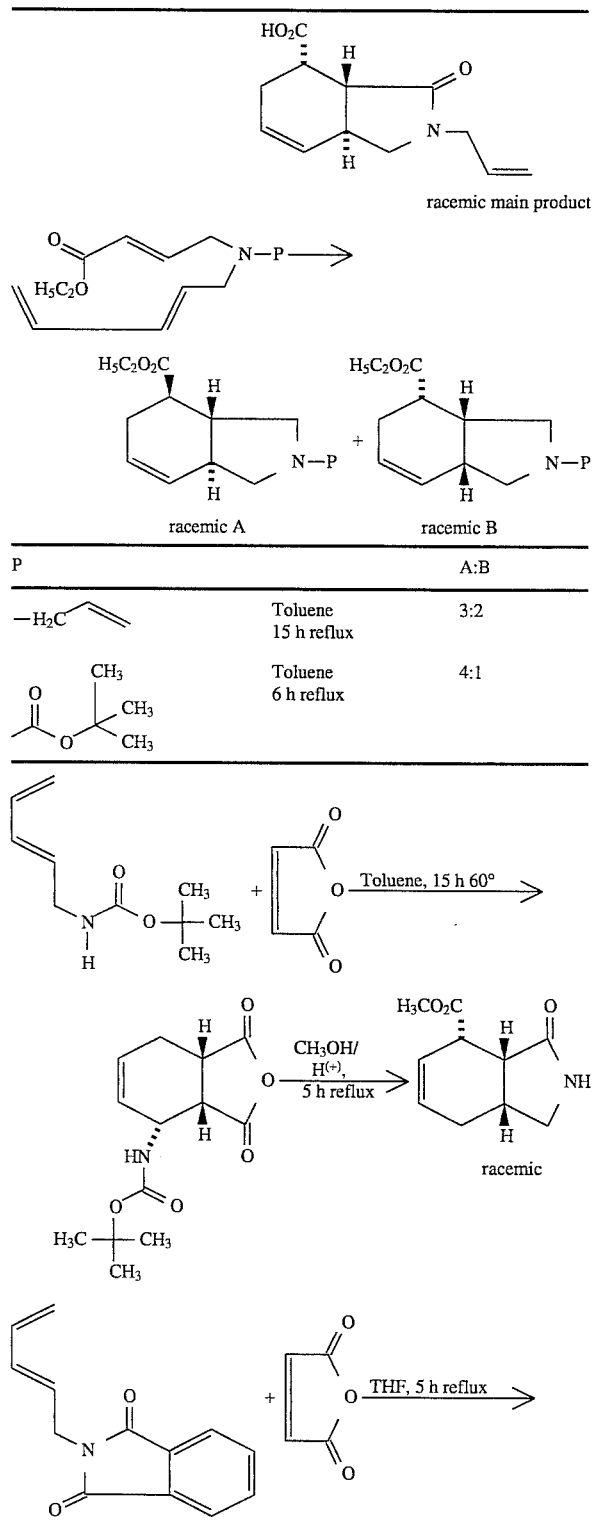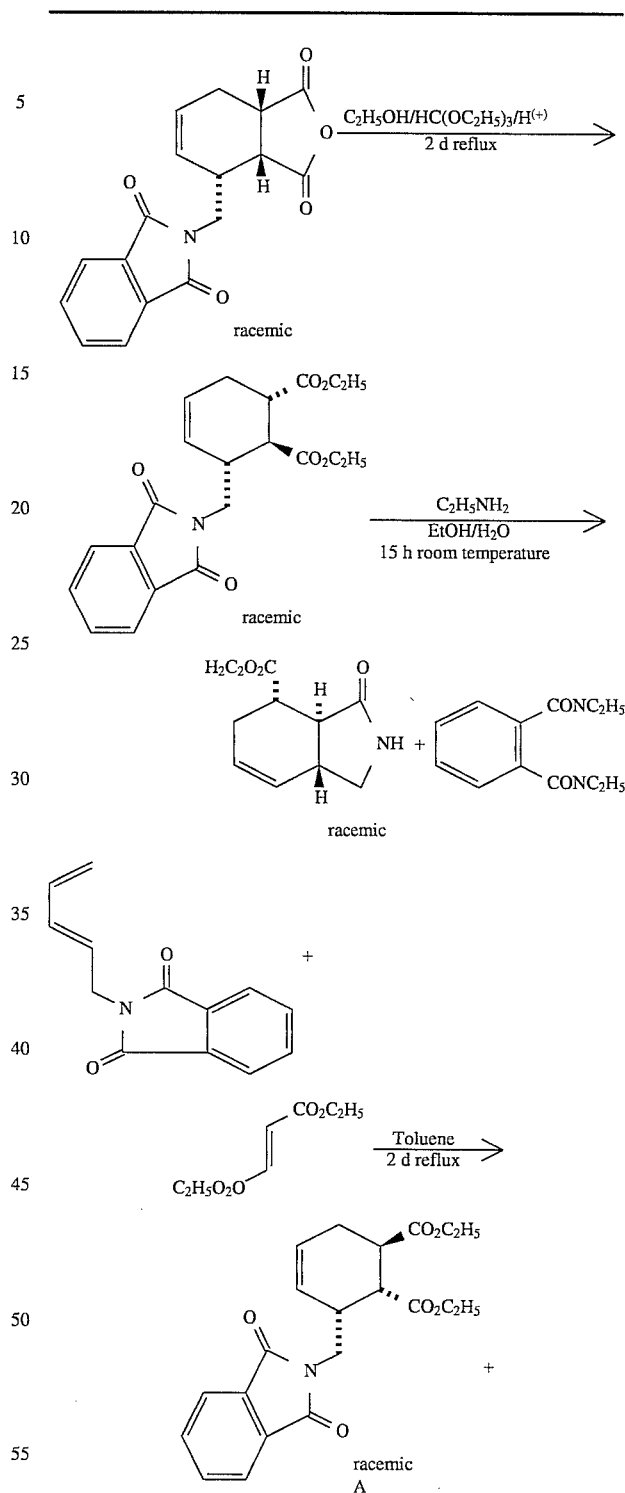

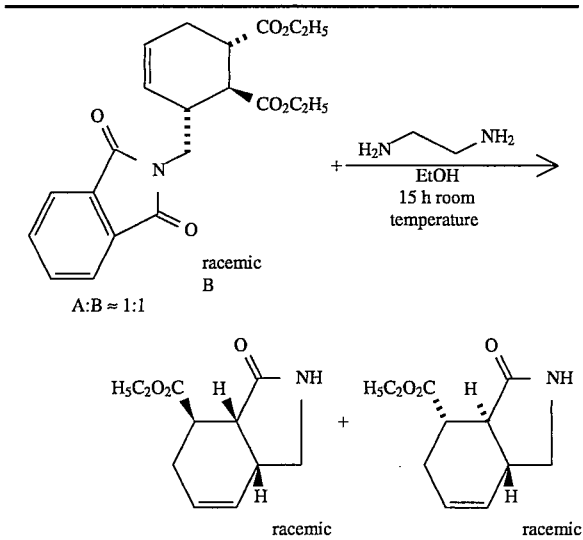

Suitable diluents for the Diels-Alder reaction are any inert organic solvents. These preferably include ethers such as diisopropyl ether, di-n-butyl ether, dimethoxyethane, tetrahydrofuran and anisole, hydrocarbons such as e.g. hexane, methylcyclohexane, toluene, xylene and mesitylene, and halogenated hydrocarbons such as e.g. chloroform, 1,2-dichloroethane and chlorobenzene. However, the Diels-Alder reaction can also be carried out without a solvent.

The reaction temperatures can be varied over a relatively wide range. The reaction is generally carried out at between about −20° C. and +200° C., preferably at between −20° C. and +150° C. The Diels-Alder reaction is normally carried out at atmospheric pressure, but it is also possible to use pressures of up to 1.5 GPa to accelerate the reaction.

The further reaction of the compounds of the formula (7) to give the compounds of the formula (8) takes place as described in the Examples or by known methods of organic chemistry.

Further reactions are required to obtain the compounds of the formula (III) from the compounds of the formula (3), (4) or (8).

Examples which may be mentioned are the hydrolysis of an ester to the carboxylic acid, the reduction of carbonyl groups, for example esters, to aldehydes or alcohols or of lactam groups to the pyrrolidines, the conversion of a hydroxyl group to an amino group, the conversion of a carboxyl group or a derivative thereof to an amine group with degradation by one carbon atom, the reductive amination of an aldehyde with an amine group present in the molecule, the reductive amination of an aldehyde group present in the molecule with an amine, the introduction of protecting groups and the cleavage of the protecting group from the pyrrolidine nitrogen in such a way that any other protecting groups present in the molecule remain intact.

These reactions take place as described in the Examples or by methods conventionally used in organic chemistry.

The further reaction of the compounds of the formula (3), (4) or (8) to give the compounds of the formula (III) can be illustrated for example by the following equations:

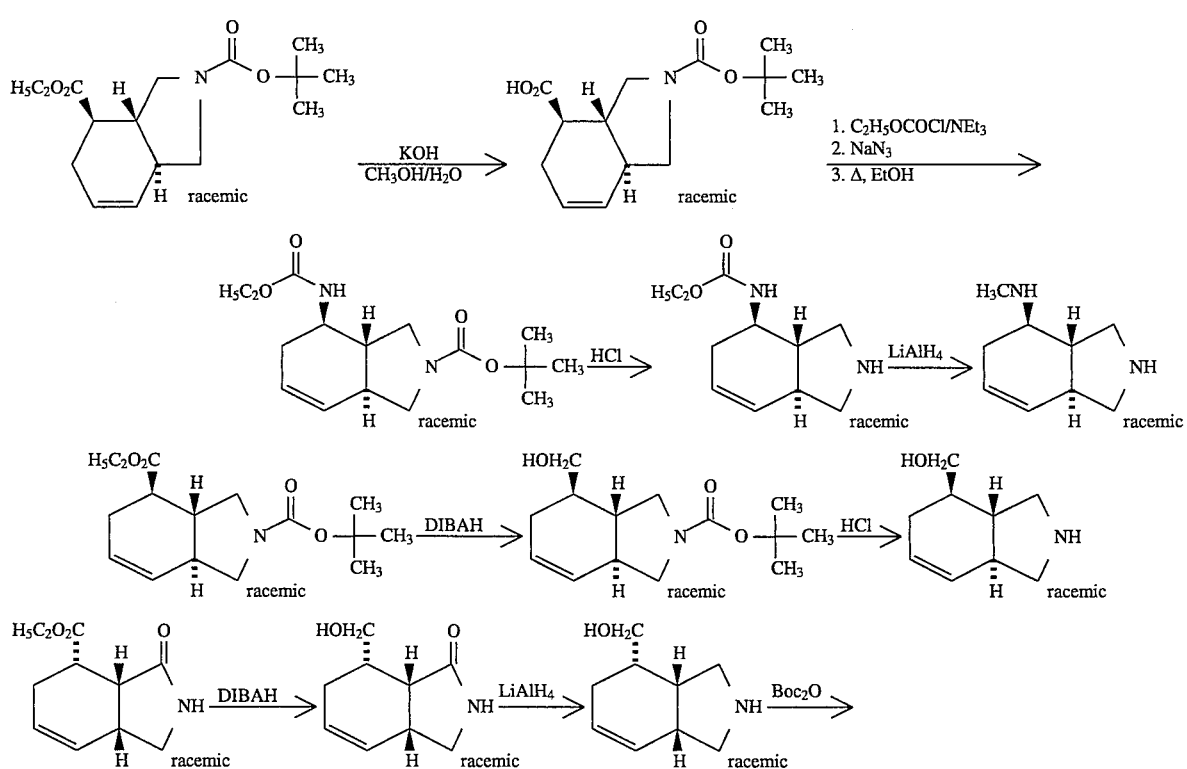

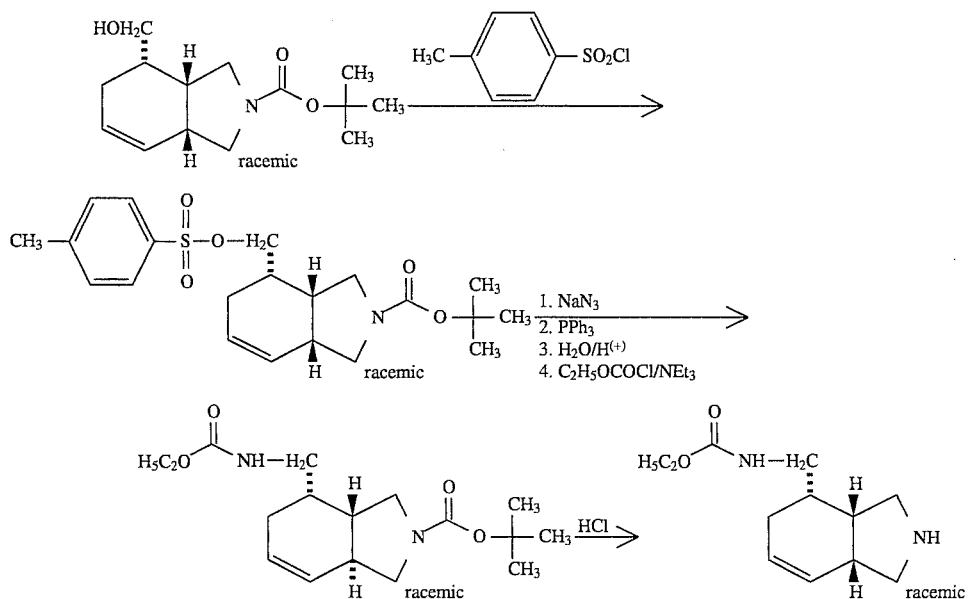

Most of the starting materials of the formulae (1), (2), (5) and (6) are known or can be prepared by known methods of organic chemistry.

The reaction of (II) with (III), in which the compounds (III) can also be used in the form of their salts, e.g. the hydrochlorides, is preferably carried out in a diluent such as dimethyl sulphoxide, N,N-dimethylformamide, N-methylpyrrolidone, hexamethylphosphorotriamide, sulpholane, acetonitrile, water, an alcohol like methanol, ethanol, n-propanol, isopropanol or glycol monomethyl ether, or pyridine. It is also possible to use mixtures of these diluents.

Acid-binding agents which can be used are any conventional inorganic and organic acid-binding agents. These preferably include alkali metal hydroxides, alkali metal carbonates and organic amines and amidines. The following may be mentioned specifically as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. The reaction is generally carried out at between about 20° and 200° C., preferably at between 80° and 180° C.

The reaction can be carried out at atmospheric pressure or else at elevated pressure. The operating pressures are generally between 1 bar and 100 bar, preferably between 1 and 10 bar.

The process according to the invention is carried out using 1 to 15 mol, preferably 1 to 6 mol, of the compound (III) per mol of the compound (II).

Free amino groups can be protected during the reaction by a suitable amino-protecting group, for example by the tert-butoxycarbonyl radical, and freed again after completion of the reaction by treatment with a suitable acid such as hydrochloric acid or trifluoroacetic acid (see Houben-Weyl, Methoden der Organischen Chemie (Methods of Organic Chemistry), volume E4, page 144 (1983); J. F. W. Mc Omie, Protective Groups in Organic Chemistry (1973), page 43).

The esters according to the invention are obtained by reacting an alkali metal salt of the corresponding carboxylic acid, which can optionally be protected on the N atom by a protecting group such as the tert-butoxycarbonyl radical, with suitable halogenoalkyl derivatives in a solvent such as dimethylformamide, dimethylacetamide, N-methylpyrrolidone, dimethyl sulphoxide or tetramethylurea, at temperatures of about 0° to 100° C., preferably 0° to 50° C.

The acid addition salts of the compounds according to the invention are prepared in conventional manner, for example by dissolving the betaine in a sufficient amount of aqueous acid and precipitating the salt with a water-miscible organic solvent such as methanol, ethanol, acetone or acetonitrile. It is also possible to heat equivalent amounts of betaine and acid in water or an alcohol such as glycol monoethyl ether and then evaporate to dryness or filter off the precipitated salt with suction. Pharmaceutically acceptable salts are to be understood as meaning for example the salts of hydrochloric acid, sulphuric acid, acetic acid, glycolic acid, lactic acid, succinic acid, citric acid, tartaric acid, methanesulphonic acid, toluene-4-sulphonic acid, galacturonic acid, gluconic acid, embonic acid, glutamic acid or aspartic acid. The compounds according to the invention can also be bound to acidic or basic ion exchangers.

The alkali metal or alkaline earth metal salts of the carboxylic acids according to the invention are obtained for example by dissolving the betaine in less than the stoichiometric amount of alkali metal or alkaline earth metal hydroxide solution, filtering off the undissolved betaine and evaporating the filtrate to dryness. Sodium, potassium or calcium salts are pharmaceutically appropriate. Reaction of an alkali metal or alkaline earth metal salt with a suitable silver salt, such as silver nitrate, gives the corresponding silver salts.

The compounds according to the invention have a potent antibiotic activity and, coupled with low toxicity, have a broad antibacterial spectrum against Gram-positive and Gram-negative germs, especially also against those which are resistant to various antibiotics, e.g. penicillins, cephalosporins, aminoglycosides, sulphonamides and tetracyclines.

These valuable properties enable said compounds to be used as chemotherapeutic action in medicine and veterinary medicine, and as substances for preserving inorganic and organic materials, especially all kinds of organic materials, e.g. polymers, lubricants, paints, fibres, leather, paper and wood, foodstuffs and water.

The compounds according to the invention are active against a very broad spectrum of microorganisms. They can be used to control Gram-negative and Gram-positive bacteria and bacterioid microorganisms and to prevent, alleviate and/or cure the diseases caused by these pathogens.

The compounds according to the invention are distinguished by an increased action on dormant and resistant germs. On dormant bacteria, i.e. bacteria which show no detectable growth, the compounds are active below the concentrations of similar substances. This applies not only to the amount to be used, but also to the rate of destruction. Such results could be observed with Gram-positive and Gram-negative bacteria, especially *Staphylococcus aureus*, *Micrococcus luteus* and *Enterococcus faecalis*.

The compounds according to the invention also exhibit surprising increases in action against bacteria which are classified as less sensitive towards comparable substances, especially resistant *Staphylococcus aureus* and *Enterococcus faecalis*.

The compounds according to the invention are particularly active against bacteria and bacterioid microorganisms. They are therefore particularly suitable in human and veterinary medicine for the prophylaxis and chemotherapy of local and systemic infections caused by these pathogens.

The compounds are also suitable for controlling infections caused by protozoa and helminths.

The compounds according to the invention can be used in various pharmaceutical formulations. Preferred pharmaceutical formulations which may be mentioned are tablets, coated tablets, capsules, pills, granules, suppositories, injectable and oral solutions, suspensions and emulsions, as well as pastes, ointments, gels, creams, lotions, powders and sprays.

The minimum inhibitory concentrations (MIC) were determined by the serial dilution method on Iso-Sensitest agar (Oxoid). For each test substance a series of agar plates were prepared which contained decreasing active ingredient concentrations obtained by progressive two-fold dilution. The agar plates were inoculated with a Multipoint inoculator (Denley). Inoculation was effected using overnight cultures of the pathogens which were diluted beforehand so that each inoculation spot contained ca. $10^4$ colony-forming particles. The inoculated agar plates were incubated at 37° C. and the germ growth was evaluated after ca. 20 hours. The MIC (μm/ml) indicates the lowest active ingredient concentration at which no growth could be observed with the naked eye.

The Table below lists the MIC of some of the compounds according to the invention in comparison with 9-fluoro-3-methyl-10-(4-methylpiperazin-1-yl)-7-oxo-2,3-dihydro-7H-pyrido[1,2,3-d,e]-[1,3,4]-benzoxadiazine-6-carboxylic acid (EP-O 259 804) as the reference compound.

TABLE

| | | MIC | | | |
|---|---|---|---|---|---|
| | | Example no. | | | Reference |
| Species | Strain | 1 | 2 | 4 | |
| E. coli | Neumann ATCC 25922 | 0.03 | ≦0.015 | ≦0.015 | ≦0.015 |
| | | 0.03 | ≦0.015 | ≦0.015 | ≦0.015 |

TABLE-continued

| | | MIC | | | |
|---|---|---|---|---|---|
| | | Example no. | | | Reference |
| Species | Strain | 1 | 2 | 4 | |
| Klebsiella pneumoniae | 8085 | 0.06 | ≦0.015 | 0.031 | 0.062 |
| | 63 | 0.06 | ≦0.015 | 0.031 | 0.062 |
| Providencia sp. | 12012 | 0.06 | ≦0.015 | 0.031 | 0.062 |
| | 12052 | 2 | 1 | 1 | 2 |
| Micrococcus luteus | 9341 | 0.125 | 0.031 | 0.062 | 2 |
| Staphylococcus aureus | ICB 23701 | 0.5 | 0.125 | 0.25 | 16 |
| | ATCC 29213 | 0.03 | ≦0.015 | ≦0.015 | 0.5 |
| | 133 | 0.03 | ≦0.015 | ≦0.015 | 0.5 |
| | ICB 25768 | 1 | 0.5 | 1 | 64 |
| Enterococcus faecalis | 27101 | 0.06 | ≦0.015 | 0.031 | 1 |
| | 9790 | 0.06 | ≦0.015 | 0.031 | 1 |

PREPARATION OF THE ACTIVE INGREDIENTS

Example 1

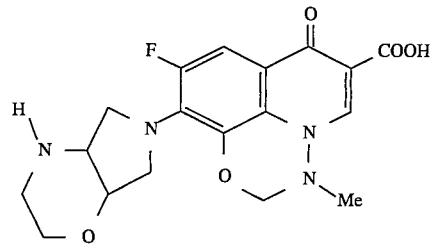

9-Fluoro-3-methyl-10-(2-oxa-5,8-diazabicyclo[4.3.0]nonan-8-yl)-7-oxo-2,3-dihydro-7H-pyrido[1,2,3-d,e][1,3,4]benzoxadiazine-6-carboxylic acid 500 mg (1.77 mmol) of 9,10-difluoro-3-methyl-7-oxo-2,3-dihydro-7H-pyrido[1,2,3-d,e][1,3,4]-benzoxadiazine-6-carboxylic acid are heated at 100° C. for eight hours with 450 mg (3.51mmol) of 2-oxa-5,8-diazabicyclo[4.3.0]nonane in 15 ml of pyridine under argon. The mixture is concentrated under high vacuum and the residue is recrystallized from ethanol and dried.

Yield: 410 mg (59% of theory)

Melting point: 260°–262° C. (with decomposition)

Example 2

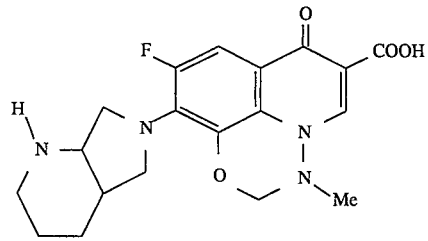

10-(2,8-Diazabicyclo[4.3.0]nonan-8-yl)-9-fluoro-3-methyl-7-oxo-2,3-dihydro-7H-pyrido[1,2,3-d,e][1,3,4]benzoxadiazine-6-carboxylic acid The title compound is obtained analogously to Example 1 by carrying out the reaction with 2,8-diazabicyclo[4.3.0]nonane.

Melting point: 256°–258° C. (with decomposition)

Example 3

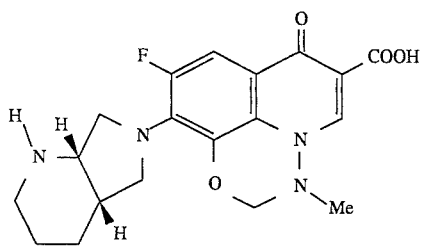

10-((1S,6S)-2,8-Diazabicyclo[4.3.0]nonan-8-yl)-9-fluoro-3-methyl-7-oxo-2,3-dihydro-7H-pyrido[1,2,3-d,e][1,3,4]benzoxadiazine-6-carboxylic acid The title compound is obtained analogously to Example 1 by carrying out the reaction with (1S,6S)-2,8-diazabicyclo[4.3.0]nonane.

Melting point: 255°–257° C.

Example 4

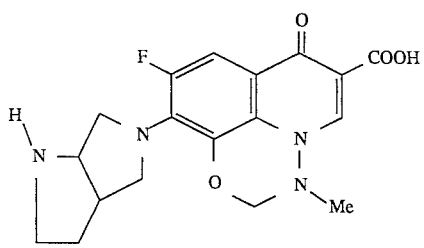

10-(2,7-Diazabicyclo[3.3.0]nonan-7-yl)-9-fluoro-3-methyl-7-oxo-2,3-dihydro-7H-pyrido[1,2,3-d,e][1,3,4]benzoxadiazine-6-carboxylic acid 100 mg (0.35 mmol) of 9,10-difluoro-3-methyl-7-oxo-2,3-dihydro-7H-pyrido[1,2,3-d,e][1,3,4]-benzoxadiazine-6-carboxylic acid are heated at 100° C. for four hours with 80 mg (0.71 mmol) of 2,7-diazabicyclo[3.3.0]nonane in 4 ml of pyridine under argon. The mixture is concentrated under high vacuum and the residue is recrystallized from ethanol and dried. The title compound obtained is contaminated with ca. 15% of a regioisomer.

Yield: 60 mg (46% of theory)
Melting point: 220°–224° C. (with decomposition)

Example 5

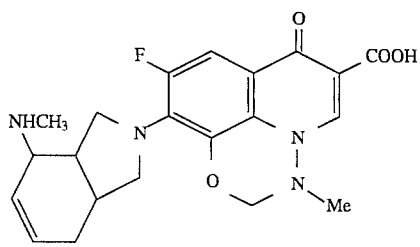

9-Fluoro-3-methyl-10-(2-methylamino-8-azabicyclo[4.3.0]-non-3-en-8-yl)-7-oxo-2,3-dihydro-7H-pyrido[1,2,3-de][1,3,4-benzoxadiazine-6-carboxylic acid 150 mg (0.53 mmol) of 9,10-difluoro-3-methyl-7-oxo-2,3-dihydro-7H-pyrido[1,2,3-de][1,3,4]-benzoxadiazine-6-carboxylic acid are heated at 100° C. for four hours with 120 mg (0.79 mmol) of 2-methylamino-8-azabicyclo[4.3.0]non-3-ene in 5 ml of pyridine under argon. The mixture is concentrated under high vacuum and the residue is recrystallized from methanol and dried.

Yield: 118 mg (54% of theory)
Melting point: 233°–235° C. (with decomposition)

Example 6

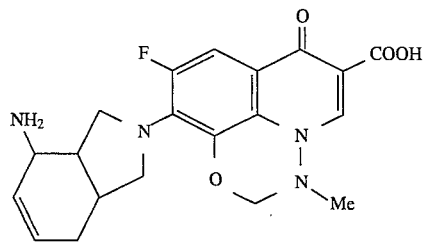

10-(2-Amino-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid The title compound is obtained analogously to Example 1 by carrying out the reaction with 2-amino-8-azabicyclo[4.3.0]non-3-ene.

Melting point: 246°–250° C. (with decomposition)

Example 7

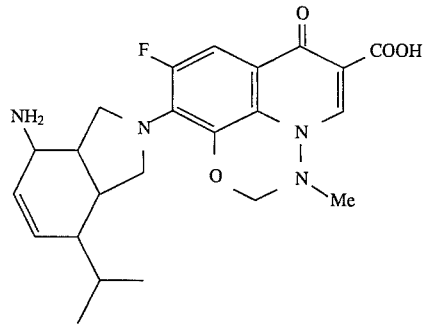

10-(2-Amino-5-isopropyl-8-azabicyclo[4.3.0]non-3-en-8-yl)-9-fluoro-3-methyl-7-oxo-2,3-dihydro-7H-pyrido[1,2,3-d,e](1,3,4]benzoxadiazine-6-carboxylic acid The title compound is obtained analogously to Example 1 by carrying out the reaction with 2-amino-5-isopropyl-8azabicyclo[4.3.0]non-3-ene.

Melting point: 194°–199° C.

Example 8

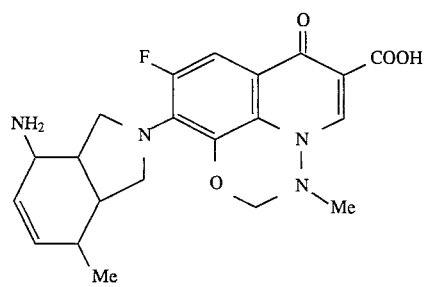

10-(2-Amino-5-methyl-8-azabicyclo[4.3.0]non-3-en-8-yl)-9-fluoro-3-methyl-7-oxo-2,3-dihydro-7H-pyrido[1,2,3-d,e][(1,3,4]benzoxadiazine-6-carboxylic acid 150 mg (0.53 mmol) of 9,10-difluoro-3-methyl-7-oxo-2,3-dihydro-7H-pyrido[1,2,3-d,e][1,3,4]benzoxadiazine-6-carboxylic acid are heated at 100° C. for 4 hours with 120 mg (0.79 mmol) of 2-amino-5-methyl-8-azabicyclo[4.3.0]non-3-ene in 5 ml of pyridine under argon. The mixture is concentrated treated under high vacuum and the residue is recrystallized from methanol/chloroform and dried.

Yield: 90 mg (41% of theory)

Melting point: 231°–233 ° C. (with decomposition)

Example 9

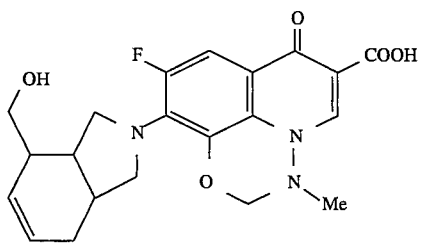

10-(2-Hydroxymethyl-8-azabicyclo[4.3.0]non-3-en-8-yl)-9-fluoro-3-methyl-7-oxo-2,3-dihydro-7H-pyrido[1,2,3]-d,e][1,3,4benzoxadiazine-6-carboxylic acid 150 mg (0.53 mmol) of 9,10-difluoro-3-methyl-7-oxo-2,3-dihydro-7H-pyrido[1,2,3-d,e][1,3,4]benzoxadiazine-6-carboxylic acid are heated at 115° C. for four hours with 120 mg (0.78 mmol) of 2-hydroxymethyl-8-azabicyclo[4.3.0]non-3-ene in 5 ml of pyridine under argon. The mixture is concentrated under high vacuum and the residue is recrystallized from methanol and dried.

Yield: 154 mg (70% of theory)

Melting point: 270°–272° C. (with decomposition)

Example 10

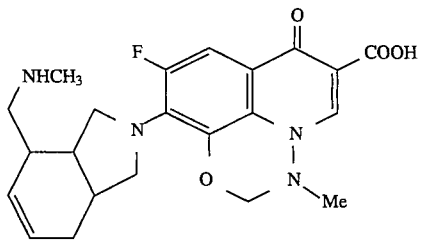

10-(2-Methylaminomethyl-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid The title compound is obtained analogously to Example 5 by carrying out the reaction with 2-methylaminomethyl-8-azabicyclo[4.3.0]non-3-ene.

Melting point: 272°–274° C. (with decomposition)

Example 11

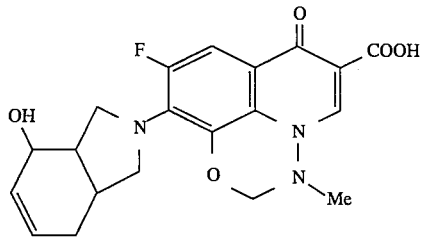

10-(2-Hydroxy-8-azabicyclo[4.3.0]non-3-en-8-yl)-9-fluoro-3-methyl-7-oxo-2,3-dihydro-7H-pyrido[1,2,3-d,e][1,3,4] benzoxadiazine-6-carboxylic acid 150 mg (0.53 mmol) of 9,10-difluoro-3-methyl-7-oxo-2,3-dihydro-7H-pyrido[1,2,3-d,e][1,3,4]benzoxadiazine-6-carboxylic acid are heated at 115° C. for fourteen hours with 110 mg (0.79mmol) of 2-hydroxy-8-azabicyclo[4.3.0]non-3-ene in 5 ml of pyridine under argon. The mixture is concentrated under high vacuum and the residue is recrystallized from methanol and dried.

Yield: 63 mg (30% of theory)

Example 12

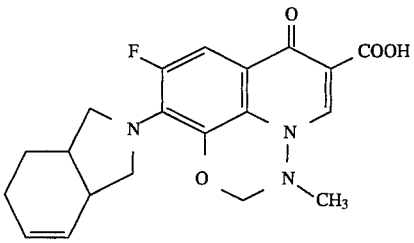

10-(8'-Azabicyclo[4.3.0]non-2'-en-8'-yl)-9-fluoro-3-methyl-7-oxo-2,3-dihydro-7H-pyrido[1,2,3-d,e][1,3,4]benzoxadiazine-6-carboxylic acid A mixture of 846 mg (3.0 mmol) of 9,10-difluoro-3-methyl-7-oxo-2,3-dihydro-7H-pyrido[1,2,3-d,e][1,3,4]benzoxadiazine-6-carboxylic acid, 553 mg (4.5 mmol) of 8-azabicyclo[4.3.0]non-2-ene (product of Example A) and pyridine (24 ml) was stirred for 4 h under nitrogen at 100° C. The mixture was concentrated under high vacuum and the crude product was stirred with methanol, filtered off with suction and dried at 60° C.

Yield: 850 mg (66% of theory).

Melting point: 309° C.

Example 13

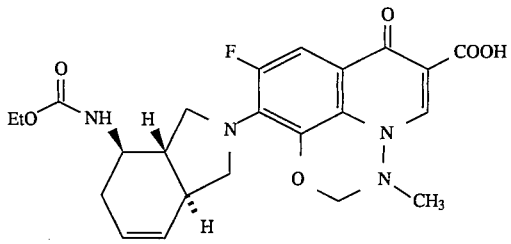

(1'SR,2'RS,6'SR)-10-(2'-Ethoxycaarbonylamino-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxylic acid A mixture of 282 mg (1.0 mmol) of 9,10-difluoro-3-methyl-7-oxo-2,3-dihydro-7H-pyrido[1,2,3-d,e][1,3,4]benzoxadiazine-6-carboxylic acid, 315 mg (1.5 mmol) of (1SR, 2RS,6SR)-2'-ethoxycarbonylamino-8-azabicyclo[4.3.0]non-4-ene (product of Example C) and 8.5 ml of pyridine is heated at 100° C. for 4 h under nitrogen. It is then concentrated under high vacuum and the residue is stirred with methanol, filtered off with suction and dried at 60° C.

Yield: 350 mg (74% of theory).

Melting point: 195° C.

Example 14

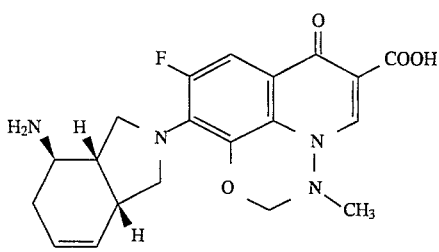

(1'SR,2'RS,6'SR)-10-(2'-Amino-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxlic acid A mixture of 480 mg (1.0 mmol) of (1'SR,2'RS,6'SR)-10-(2'-ethoxycarbonylamino-8'-azabicyclo[4.3.1]non-4'-en-8'-yl)-9-fluoro-3-methyl-7-oxo-2,3-dihydro-7H-pyrido[1,2,3-d,e][1,3,4]benzoxadiazine-6-carboxylic acid (product of Example II), 640 mg (2.0 mmol) of barium hydroxide octahydrate, methanol (5 ml) and water (2.5 mmol) is heated at 80° C. for 4 h. The same amount of solvent is added again and the mixture is stirred for a further 36 h at 80° C. After cooling, the precipitate is filtered off with suction, washed with a small amount of methanol and water and dried. The solid obtained is suspended in 5 ml of water and acidified with 1N hydrochloric acid. The residual solid is filtered off with suction and dried.

Yield: 400 mg (98% of theory).
Melting point: >300° C.

Example 15

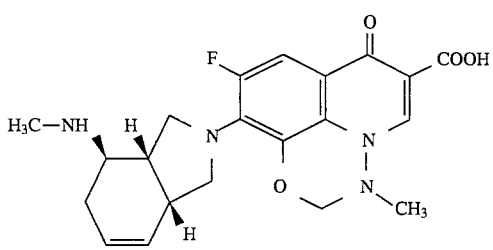

(1'SR,2'RS,6'RS)-9-Fluoro-3-methyl-10-(2'-methylamino-8'-azabicyclo[4.3.0]non-4'-en-8'-yl)-7-oxo-2,3-dihydro-7H-pyrido[1,2,3-d,e][1,3,4]-benzoxadiazine-6-carboxylic acid 282 mg (1.0 mmol) of 9,10-difluoro-3-methyl-7-oxo-2,3-dihydro-7H-pyrido[1,2,3-d,e][1,3,4]benzoxadiazine-6-carboxylic acid and 228 mg (1.5 mmol) of (1SR,2RS,6RS)-2-methylamino-8-azabicyclo[4.3.0]non-4-ene (product of Example N) are reacted in 8.5 ml of pyridine as described in Example 12.

Yield: 250 mg (61% of theory).
Melting point: 293° C.

Example 16

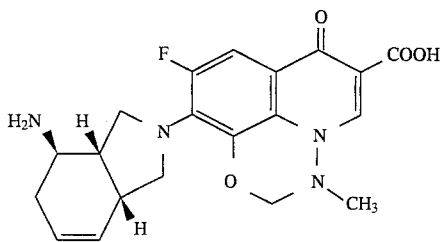

(1'SR,2'RS,6'RS)-10-(2'-Amino-8'-azabicyclo[4.3.0]non-4'-en-8'-yl)-9-fluoro-3-methyl-7-oxo-2,3-dihydro-7H-pyrido[1,2,3-d,e][1,3,4]-benzoxadiazine-6-carboxylic acid 455 mg (1.6 mmol) of 9,10-difluoro-3-methyl-7-oxo-2,3-dihydro-7H-pyrido[1,2,3-d,e][1,3,4]benzoxadiazine-6-carboxylic acid and 300 mg (2.1 mmol) of 2-amino-8-azabicyclo[4.3.0]non-4-ene were reacted in 10 ml of pyridine as described in Example 12.

Yield: 500 mg (78% of theory).
Melting point: 233° C.

Example 17

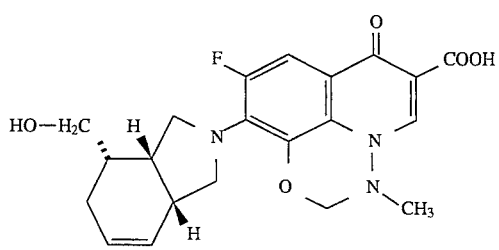

(1'SR,2'SR, 6'RS)-9-Fluoro-10-(2'-hydroxymethyl-8'-azabicyclo[4.3.0]non-4'-en-8'-yl)-3-methyl-7-oxo-2,3-dihydroxy-7H-pyrido[1,2,3-d,e][1,3,4]benzoxadiazine-6-carboxylic acid 845 mg (3.0 mmol) of 9,10-difluoro-3-methyl-7-oxo-2,3-dihydro-7H-pyrido[1,2,3-d,e][1,3,4]benzoxadiazine-6-carboxylic acid and 690 mg (4.5 mmol) of 2-hydroxymethyl-8-azabicyclo[4.3.0]non-4-ene were reacted in 24 ml of pyridine as described in Example 12.

Yield: 650 mg (52% of theory).
Melting point: 240° C.

Example 18

(1'SR,2'SR,6'RS)-10-(2'-Amino-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxylic acid 425 mg (1.5 mmol) of 9,10-difluoro-3-methyl-7-oxo-2,3-dihydro-7H-pyrido[1,2,3-d,e][1,3,4]benzoxadiazine-6-carboxylic acid and 270 mg (20 mmol) of 2-amino-8-azabicyclo[4.3.0]non-4-ene were reacted in 10 ml of pyridine as described in Example 12.

Yield: 400 mg (67% of theory).
Melting point: 242° C.

Example 19

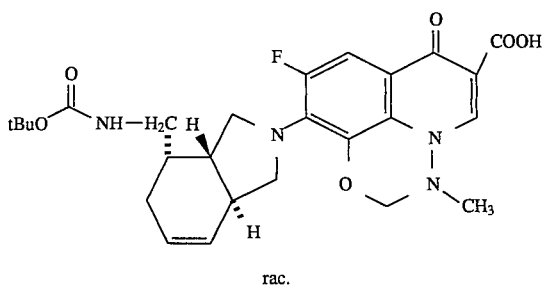

rac.

(rac.=racemate)
(1'SR,2'SR,6'SR)-10-(2'-tert-Butoxycarbonylamino-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxylic acid 469 mg (1.7 mmol) of 9,10-difluoro-3-methyl-7-oxo-2,3-dihydro-7H-pyrido[1,2,3-d,e][1,3,4]benzoxadiazine-6-carboxylic acid and 665 mg (2.5 mmol) of 2-tert-butoxycarbonylamino-8-azabicyclo[4.3.0]non-4-ene were reacted in 15 ml of pyridine as described in Example 12.
Yield: 550 mg (64% of theory).

Example 20

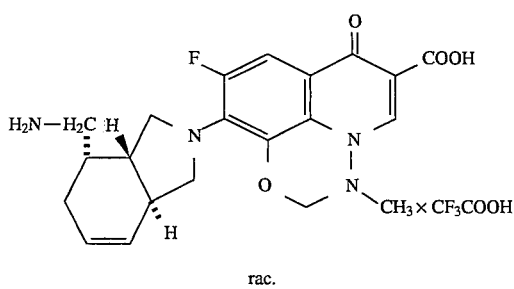

rac.

(rac.=racemate)
(1'SR,2'SR,6'SR)-10-(2'-Amino-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxylic acid trifluoroacetate 500 mg (9.0 mmol) of the title compound of Example 19 are suspended in 10 ml of ice-cooled trifluoroacetic acid and allowed to warm up to room temperature. After 1 h at room temperature, the product is precipitated with methanol, filtered off with suction and dried at 50° C.
Yield: 500 mg (90% of theory).
Melting point: 247° C. (decomposition).

Example 21

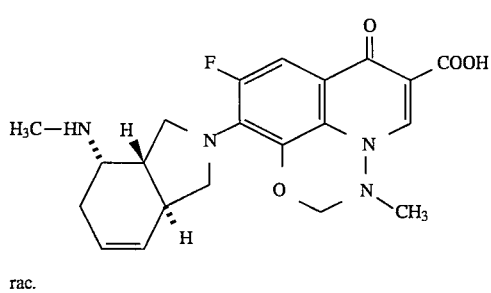

rac.

(rac.=racemate)
(1'SR,2'SR,6'SR)-9-Fluoro-3-methyl-10-(2'-methylamino-8'-azabicyclo[4.3.0]non-4'-en-8'-yl)-7-oxo-2,3-dihydro-7H-pyrido[1,2,3-d,e][1,3,4]benzoxadiazine-6-carboxylic acid 455 mg (1.6 mmol) of 9,10-difluoro-3-methyl-7-oxo-2,3-dihydro-7H-pyrido[1,2,3-d,e][1,3,4]benzoxadiazine-6-carboxylic acid and 319 mg (2.1 mmol) of 2-methylamino-8-azabicyclo[4.3.0]non-4-ene were reacted in 10 ml of pyridine as described in Example 12.
Yield: 650 mg (98% of theory).
Melting point: 247° C.

Example 22

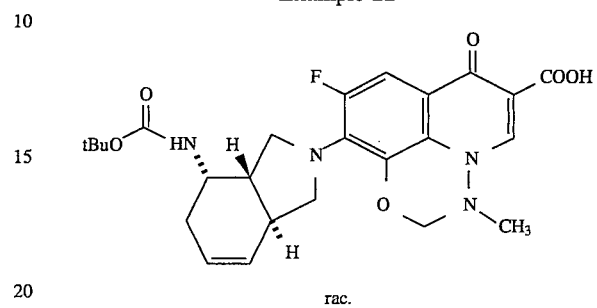

rac.

(rac.=racemate)
(1'SR,2'SR,6'SR)-10-[2'-(tert-Butoxycarbonylamino)methyl-8'-azabicyclo[4.3.0]non-4'-en-8'-yl]-9-fluoro-3-methyl-7-oxo-2,3-dihydro-7H-pyrido[1,2,3-d,e][1,3,4]benzoxadiazine-6-carboxylic acid 469 mg (1.7 mmol) of 9,10-difluoro-3-methyl-7-oxo-2,3-dihydro-7H-pyrido[1,2,3-d,e][1,3,4]benzoxadiazine-6-carboxylic acid and 595 mg (2.5 mmol) of 2-(tert-butoxycarbonylamino)methyl-8-azabicyclo[4.3.0]non-4-ene were reacted in 15 ml of pyridine as described in Example 12.
Yield: 580 mg (59% of theory).

Example 23

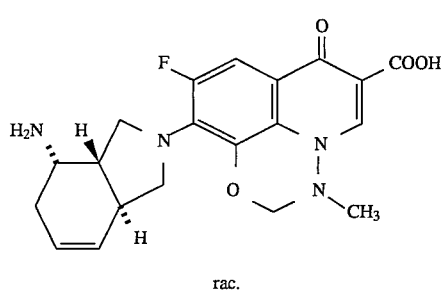

rac.

(rac.=racemate)
(1'SR,2'SR,6'SR)-10-(2'-Aminomethyl-8'-azabicyclo[4.3.0]non-4'-en-8'-yl)-9-fluoro-3-methyl-7-oxo-2,3-dihydro-7H-pyrido[1,2,3-d,e][1,3,4]benzoxadiazine-6-carboxylic acid trifluoroacetate 500 mg (1.0 mmol) of the title compound of Example 22 are reacted with 10 ml of trifluoroacetic acid as described in Example 20.
Yield: 480 mg (88% of theory).
Melting point.: 251° C. (decomposition).
Melting point: 248°–250° C. (with decomposition)

Preparation of the Intermediates

Example A

8-Azabicyclo[4.3.0]non-2-ene
A.1. (E)-1-Bromo-2,4-pentadiene

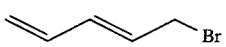

The starting material is 84 g (1.0 mol) of 1,4-pentadiene-3-ol at 0° C. 150 ml (≈1.3 mol) of 48% aqueous hydrobromic acid are added dropwise, with stirring, so that the internal temperature does not exceed 5° C. When the addition is complete, stirring is continued for 1 h at room temperature. The organic phase is separated off and reacted further without purification.

Yield: 107–129 g (73–88% of theory)

A.2. (E)-1-(2-Propenylamino)-2,4-pentadiene

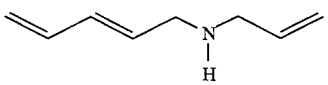

The starting material is 228 g (4.0 mol) of 1-amino-2-propene. 58.8 g (0.4 mol) of (E)-1-bromo-2,4-pentadiene (title compound of Example A.1.) are added dropwise, with stirring. The internal temperature is kept in the range 20°–30° C. by cooling. The reaction mixture is stirred for 5 h at room temperature and concentrated at 150 mbar. A solution of 20 g (0.5 mol) of sodium hydroxide in 200 ml of water is added, the mixture is extracted with twice 100 ml of methylene chloride, the extracts are dried over sodium sulphate, 0.1 g of 4-hydroxyanisole is added and the mixture is concentrated and distilled at 40 mbar. The distillate is stabilized by the addition of 10–20 ppm of 4-hydroxyanisole.

Yield: 33–35 g (67–72% of theory)

Boiling point: 77°–82° C. at 40 mbar $^1$H NMR (CDCl$_3$): δ6.07–6.48 (m, 2H); 5.64–6.07 (m, 2H); 5.00–5.27 (m, 4H); 3.19–3.36 ppm (m, 4H).

A.3. N-[(E)-2,4-Pentadienyl]-N-(2-propenyl)-acetamide

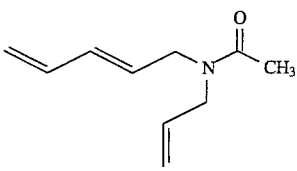

The starting material is 24.6 g (0.2 mol) of (E)-1-(2-propenylamino)-2,4-pentadiene (title compound of Example A.2.). 22.4 g of acetic anhydride are added dropwise and the mixture is stirred overnight at room temperature. It is concentrated and the crude product is reacted further.

A.4. 8-Acetyl-8-azabicyclo[4.3.0]non-2-ene

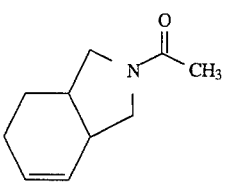

33.1 g (0.2 mol) of N-[(E)-2,4-pentadienyl]-N-(2-propenyl)-acetamide (title compound of Example A.3.) are dissolved in 200 ml of xylene, a vigorous stream of nitrogen is passed through for 15 min., 0.1 g of 4-hydroxyanisole is added and the mixture is then refluxed overnight. It is concentrated and distilled under high vacuum.

Yield: 23.1 g (70% of theory, based on the title compound of Example A.2.)

Boiling point: 88°–93° C. at 0.05 mbar

A. 5.8-Azabicyclo[4.3.0]non-2-ene

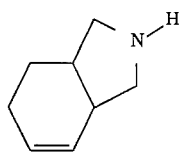

16.5 g (0.1 mol) of 8-acetyl-8-azabicyclo[4.3.0]non-2-ene (title compound of Example A.4.) are refluxed for 3 h in a mixture of 100 ml of 45% sodium hydroxide solution, 50 ml of water and 100 ml of 1,2-ethanediol. After cooling, the mixture is extracted with four times 50 ml of diethyl ether. The combined organic phases are dried over sodium sulphate and distilled under high vacuum.

Yield: 6.6 g (54% of theory)

Boiling point: 36°–44° C. at 0.35 mbar $^1$H NMR (CDCl$_3$): δ=5.79 (m, 1H); 5.74 (m, 1H); 3.02–3.17 (m, 2H); 2.47–2.72 (m, 2H); 2.06–2.30 (m, 2H); 1.91–2.06 (m, 2H); 1.68 (m, 1H); 1.45 ppm (m, 1H).

Example B

Ethyl (1RS,2RS,6SR)-8-azabicyclo[4.3.0]non-4-ene-2-carboxylate (diastereoisomer A) and
ethyl (1RS,2RS,6RS)-8-azabicyclo[4.3.0]non-4-ene-2-carboxylate (diastereoisomer B)

B.1. N-[(E)-2,4-Pentadienyl]-phthalamide

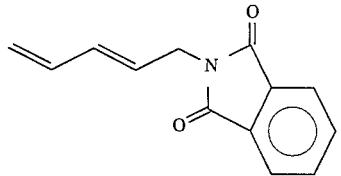

185 g (1.0 mol) of potassium phthalimide are placed in 800 ml of DMF. 147 g (1.0 mol) of (E)-1-bromo-2,4-pentadiene (title compound of Example A.1.) are added dropwise, with stirring, the internal temperature being kept below 30° C. by cooling. The reaction mixture is stirred overnight at room temperature and then poured onto 1.6 l of ice-water, with stirring, and the precipitate is filtered off with suction, washed with water and dried to constant weight at room temperature.

Yield: 177–200 g (83–94% of theory)

Melting point: 118°–121° C. (sample recrystallized from ethanol)

$^1$H NMR (CDCl$_3$): δ=7.85 and 7.72 (m, 4H, aryl-H); 6.2–6.4 (m, 2H, H on C-3 and C-4); 5.75 (dt, 1H, H on C-2, J=14 and 6 Hz); 5.20 (d, 1H, H$_a$ on C-5, J=15 Hz); 5.10 (d, 1H, H$_b$ on C-5, J=8 Hz); 4.33 ppm (d, 2H, H on C-1, J=6 Hz).

B.2. (E)-1-amino-2,4-pentadiene

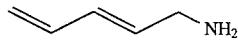

400 g of bis-(2-aminoethyl)-amine and 213 g (1.0 mol) of N-[(E)-2,4-pentadienyl]-phthalimide (title compound of Example B.1.) are placed in a 2 l distillation apparatus equipped with a 10 cm Vigreux column, and heated to the boil at 60 mbar. The product distils in the range 45°–60° C. at 60 mbar. The distillate is stabilized by the addition of 10–20 ppm of 4-hydroxyanisole.

Yield: 71–80 g (86–96% of theory)

B.3. Ethyl (E)-4-[(E)-2,4-pentadienylamino]-2-butenoate

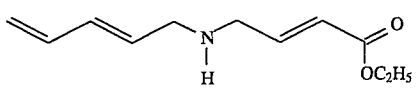

41.6 g (0.5 mol) of (E)-1-amino-2,4-pentadiene (title compound of Example B.2.) and 50.6 g (0.5 mol) of triethylamine are placed in 250 ml of THF at 0° C. and a solution of 96.5 g (0.5 mol) of ethyl (E)-4-bromo-2-butenoate in 250 ml of THF is added dropwise. The internal temperature is kept below 5° C. by cooling with ice. The mixture is stirred for 5 h at 0° C. and then overnight at room temperature. 500 ml of MTBE and then 500 ml of 1M sodium hydroxide solution are added, the mixture is shaken, the phases are separated, the aqueous phase is extracted once with 100 ml of MTBE, the combined organic phases are dried over sodium sulphate, 100 ml of toluene and 0.1 g of 4-hydroxyanisole are added and the mixture is concentrated (temperatures above 40° C. being avoided). The residue is purified by column chromatography on 1 kg of silica gel (63–200 μm) with cyclohexane/acetone 2:1. A further 0.1 g of 4-hydroxyanisole is added and the mixture is concentrated, temperatures above 40° C. being avoided.

Yield: 52.7–58.6 g (54–60% of theory) of a yellowish oil Rf=0.24.

$^1$H NMR (CDCl$_3$): δ=6.99 (dt, 1H, J=15 and 5.5 Hz); 6.1–6.45 (m, 2H); 5.98 (d, 1H, J=15 Hz); 5.75 (dt, 1H, J=15 and 6.5 Hz), 5.18 (d, 1H, J=15 Hz); 5.06 (d, 1H, J=10 Hz); 4.19 (q, 2H); 3.42 (dd, 2H); 3.31 (d, 2H); 1.29 ppm (t, 3H).

B.4. Ethyl (1RS,2RS,6SR)-8-tert-butoxycarbonyl-8-azabicyclo[4.3.0]non-4-ene-2-carboxylate (diastereoisomer A) and
ethyl (1RS,2RS,6RS)-8-tert-butoxycarbonyl-8-azabicyclo[4.3.0]non-4-ene-2-carboxylate (diastereoisomer B).

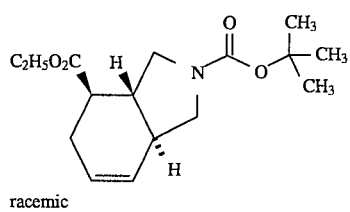

racemic

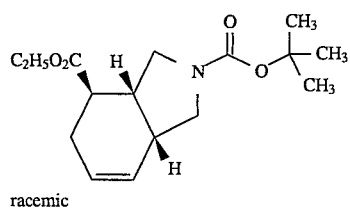

racemic

The starting material is a solution of 97.5 g (0.5 mol) of ethyl (E)-4-[(E)-2,4-pentadienylamino]-2-butenoate (title compound of Example B.3.) in 250 ml of toluene. A solution of 114.5 g (0.525 mol) of di-tert-butyl dicarbonate in 250 ml of toluene is added dropwise and the mixture is stirred overnight at room temperature. A vigorous stream of nitrogen is then passed through for 15 min, 0.1 g of 4-hydroxyanisole is added and the mixture is then refluxed for 6 h. It is concentrated and the residue is purified by column chromatography on 1 kg of silica gel (63–200 μm) with cyclohexane/acetone 8:1.

Yield: 109–134 g (74–91% of theory) of a yellowish oil; mixture of two diastereoisomers, A and B, in the ratio A:B=4:1. Rf=0.25.

$^1$H NMR (Cl$_2$DC-CDCl$_2$; 80° C.): δ=5.77 (m, 1H(A) and 1H(B)); 5.68 (m, 1H(A) and 1H(B)); 4.14 (m, 2H(A) and 2H(B)); 3.65 (m, 2H(A) and 1H(B)); 3.48 (dd, 1H(B)); 3.27 (dd, 1H(B)); 3.00 (m, 1H(A) and 1H(B)); 2.85 (dd, 1H(A)); 2.76 (m, 1H(B)); 2.60 (m, 1H(A)); 2.25–2.55 (m, 3H(A) and 4H(B)); 1.93 (m, 1H(A)); 1.51 (s, 9H(B)); 1.44 (s, 9H(A)); 1.25 ppm (t, 3H(A) and 3H(B)).

B.5. Ethyl (1RS,2RS,6SR)-8-azabicyclo[4.3.0]non-4-ene-2-carboxylate (diastereoisomer A) and
ethyl (1RS,2RS,6RS)-8-azabicyclo[4.3.0]non-4-ene-2-carboxylate (diastereoisomer B)

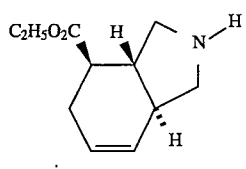

racemic

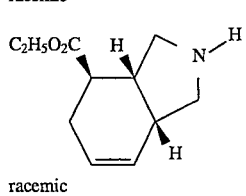

racemic 6.0 g (20 mmol) of the title compound of Example B.4. are placed in 20 ml of dioxane. 20 ml of concentrated hydrochloric acid are added dropwise, with cooling, so that the internal temperature does not exceed 30° C. When the addition is complete, the mixture is stirred for 10 min. 40 ml of methylene chloride are added and 40 ml of ice-cooled 20% sodium hydroxide solution are added dropwise, with ice-cooling. The organic phase is separated off, the aqueous phase is extracted once with methylene chloride and the combined organic phases are dried over sodium sulphate and concentrated. 3.0 g of crude product are purified by column chromatography on 100 g of silica gel (63–200 μm) with cyclohexane/ethanol/17% aqueous ammonia (1:2:0.1).

Yield: 0.8 g of diastereoisomer A and 0.8 g of diastereoisomer B Rf=0.79 for title compound of Example B.4. 0.21 for diastereoisomer B 0.11 for diastereoisomer A $^1$H NMR (CDCl$_3$): Diastereoisomer A: δ=5.83 (d, 1H); 5.69 (m, 1H); 4.15 (q, 2H); 3.21–3.38 (m, 2H); 2.52–2.89 (m, 3H); 2.21–2.52 (m, 3H); 1.95 (m, 1H); 1.28 ppm (t, 3H). Diastereoisomer B: δ=5.64–5.87 (m, 2H); 4.16 (q, 2H); 3.14–3.33 (m, 2H); 2.82 (dd, 1H); 2.15–2.74 (m, 6H); 1.28 ppm (t, 3H).

Example C (1SR,2RS,6SR)-2-Ethoxycarbonylamino-8-azabicyclo[4.3.0]non-4-ene
C.1. (1RS,2RS,6SR)-8-Tert-butoxycarbonyl-8-azabicyclo[4.3.0]non-4-ene-2-carboxlic acid

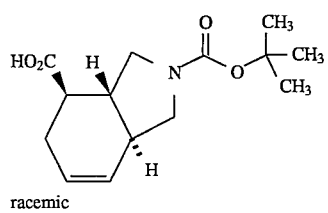

racemic

The starting material is a solution of 30.8 g (0.55 mol) of potassium hydroxide in 500 ml of water. A solution of 147.7 g (0.5 mol) of the title compound of Example B.4. in 500 ml of methanol is added and the mixture is stirred for 8 h at 60° C. under a nitrogen atmosphere. After cooling, the reaction solution is diluted with 500 ml of water, and 125 ml of acetic acid are poured in slowly, with stirring. When the addition is complete, the mixture is left to stand for 30 rain in an ice bath and the precipitate is filtered off with suction, washed with water and dried to constant weight at 50° C.

Yield: 84–98 g (63–73% of theory)

Melting point: 174°–176° C. (sample recrystallized from isopropanol/water 1:1)

$^1$H NMR (Cl$_2$DC-CDCl$_2$; 80° C.): δ=5.83 (m, 1H, H on C-5); 5.74 (m, 1H, H on C-4); 3.65–3.80 (m, 2H, H$_a$ on C-7 and H$_a$ on C-9); 3.09 (dd, 1H, H$_b$ on C-9); 2.92 (dd, 1H, H$_b$ on C-7); 2.70 (m, 1H, H on C-2); 2.35–2.60 (m, 3H, H$_a$ and H$_b$ on C-3 and H on C-6); 2.01 (m, 1H, H on C-1); 1.5 ppm (s, 9H).

C.2. (1SR,2RS,6SR)-8-Tert-butoxycarbonyl-2-ethoxycarbonylamino-8-azabicyclo[4.3.0]non-4-ene

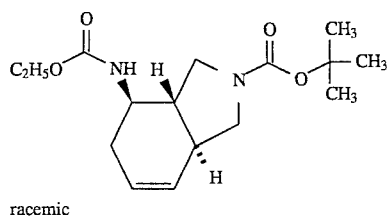

racemic

The starting material is a solution of 53.3 g (0.2 mol) of the title compound of Example C.1. and 22.2 g (0.22 mol) of triethylamine in 200 ml of anhydrous THF. With cooling with an ice/salt mixture, a solution of 22.8 g (0.21 mol) of ethyl chloroformate in 40 ml of THF is added dropwise so that the internal temperature does not exceed −10° C. When the addition is complete, the mixture is stirred for 1 h at low temperature. An ice-cooled solution of 15.6 g (0.24 mol) of sodium azide in 50 ml of water is then added dropwise, with vigorous stirring, so that the internal temperature does not exceed −10° C. When the addition is complete, the mixture is stirred for 30 min at low temperature. 300 ml of water and 400 ml of toluene are then added in succession.

The organic phase is separated off, dried over sodium sulphate and concentrated at 15mbar to half the original volume (bath temperature below 25° C.). 100 ml of ethanol are added and the mixture is heated slowly (to the extent that the evolution of nitrogen allows), with stirring, and, when the evolution of nitrogen has ceased, refluxed for 4 h. It is concentrated and the crude product is recrystallised from methanol/water 85:15 and dried to constant weight at 50° C.

Yield: 24.2–28.5 g (39–46% of theory) of the title compound

Melting point: 120°–122° C.

$^1$H NMR (CDCl$_3$): δ=5.78 and 5.73 (2d, 1H, H on C-5); 5.64 (m, 1H, H on C-4); (4.59 bs, 1H, NH); 4.12 (m, 2H, ethoxy-CH$_2$); 3.90 (m, 1H, H on C-2); 3.74 and 3.67 (2m, 1H, H$_a$ on C-7); 3.67 and 3.56 (2m, 1H, H$_a$ on C-9); 3.12 (m, 1H, H$_b$ on C-9); 2.92 (m, 1H, H$_b$ on C-7); 2.67 (m, 1H, H$_a$ on C-3); 2.49 (m, 1H, H on C-6); 1.95 (m, 1H, H$_b$ on C-3); 1.83 (m, 1H, H on C-1); 1.46 (s, 9H); 1.24 ppm (m, 3H, ethoxy-CH$_3$).

The aqueous phase is adjusted to pH 2–3 by the addition of 10% hydrochloric acid and left to stand for 30 min in an ice bath and the precipitate is filtered off with suction, washed with water and dried to constant weight at 50° C.

Yield: 16.0–19.2 g (30–36% of the title compound of Example C.1.) (recovered starting compound)

C.3. (1SR,2RS,6SR)-2-Ethoxycarbonylamino-8-azabicyclo[4.3.0]non-4-ene

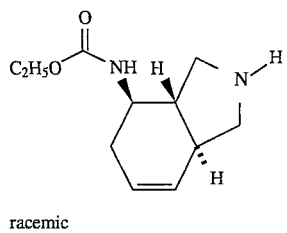

racemic 31.0 g (0.1 mol) of the title compound of Example C.2. are placed in 100 ml of a methanol/water mixture (1:1) (suspension). 100 ml of concentrated hydrochloric acid are run in rapidly (slightly exothermic up to about 40° C. (to give a homogeneous solution) and the solution is stirred until the evolution of gas has ceased (about 10 min). 200 ml of ice-water are added and 70 ml of 45% sodium hydroxide solution are added dropwise, with stirring and ice-cooling. The mixture is extracted with four times 50 ml of methylene chloride, the combined organic phases are dried over sodium sulphate and concentrated and the solvent residues are stripped off under high vacuum. The substance solidifies on concentration.

Yield: 13.7–16.6 g (65–79% of theory) of a brownish pink, amorphous solid Rf=0.81 for title compound of Example C.2. 0.11 for title compound Methylene chloride/methanol/17% aqueous ammonia (15:4:0.5)

$^1$H NMR (CDCl$_3$): δ=5.78 (d, 1H, H on C-5); 5.63 (m, 1H, H on C-4); 4.94 (bd, 1H, NH); 4.10 (m, 2H, ethoxy-CH$_2$); 3.88 (m, 1H, H on C-2); 3.28 (m, 1H, H$_a$ on C-7); 3.19 (m, 1H, H$_a$ on C-9); 2.84 (m, 1H, H$_b$ on C-9); 2.57–2.62 (m, 2H, H$_a$ on C-3 and H$_b$ on C-7); 2.43 (m, 1H, H on C-6); 1.95 (m, 1H, H$_b$ on C-3); 1.79 (m, 1H, H on C-1); 1.23 ppm (m, 3 H, ethoxy-CH$_3$).

Example D (1SR,2RS,6SR)-2-Methylamino-8-azabicyclo[4.3.0]non-4-ene

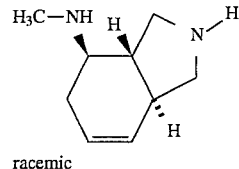

racemic 1.9 g (50 mmol) of lithium aluminium hydride are placed in 25 ml of anhydrous diethyl ether under a nitrogen atmosphere. A solution of 5.25 g (25 mmol) of the title compound of Example C.3. in 50 ml of anhydrous tetrahydrofuran is added dropwise and the mixture is refluxed for 3 h. A further 0.95 g (25 mmol) of lithium aluminium hydride is added and refluxing is continued for 3 h. Water is slowly added dropwise, with ice-cooling, until a white precipitate has formed. The precipitate is filtered off with suction and extracted by boiling with twice 100 ml of ethanol. The ethanol extracts are combined with the mother liquor from the reaction, 50 ml of toluene are added, the mixture is concentrated and the solvent residues are stripped off under high vacuum.

Yield: 1.95 g (77% of theory) of an amorphous solid Rf=0.11 Methylene chloride/methanol/17% aqueous ammonia (2:4:1)

$^1$H NMR (CDCl$_3$): δ=5.77 (d, 1H, H on C-5); 5.67 (m, 1H, H on C-4); 3.33 (dd, 1H, H$_a$ on C-7); 3.26 (dd, 1H, H$_a$ on C-9); 2.73–2.82 and 2.54–2.63 (2m, 4H, H on C-2, H$_a$ on C-3, $H_b$ on C-7 and $H_b$ on C-9); 2.41 (s, 3H, $CH_3N$); 2.34 (m, 1H, H on C-6); 1.90 (m, 1H, $H_b$ on C-3); 1.70 ppm (m, 1H, H on C-1).

Example E (1RS,2RS,6SR)-2-Hydroxymethyl-8-azabicyclo[4.3.0]non-4-ene

E. 1. (1RS,2RS,6SR)-8-Tert-butoxycarbonyl-2-hydroxymethyl-8-azabicyclo[4.3.0]non-4-ene (diastereoisomer, A) and
(1RS,2RS,6RS)-8-tert-butoxycarbonyl-2-hydroxymethyl-8-azabicyclo[4.3.0]non-4-ene (diastereoisomer B)

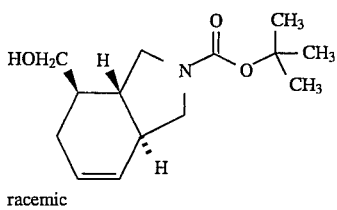
racemic A

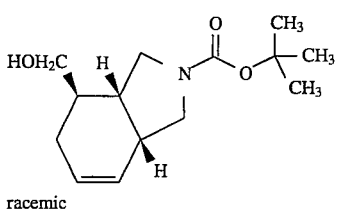
racemic B 29.5 g (0.1 mol) of the title compound of Example B.4. are placed in 200 ml of anhydrous 1,2-dimethoxyethane under a nitrogen atmosphere. 150 ml of a 1.5M solution of DIBAH in toluene (0.225 mol) are added dropwise at an internal temperature of <−65° C. When the addition is complete, the cooling bath is removed and the mixture is left to warmup to room temperature. It is then stirred for 2 h at room temperature.

60 ml of methanol are added dropwise, with vigorous stirring (exothermic reaction); the internal temperature is kept at between 35° and 45° C. by cooling with a cold water bath. 20 ml of 5% sodium hydroxide solution are then added dropwise. When the addition is complete, the mixture is stirred for 10 min. The precipitate is filtered off with suction and extracted by boiling with twice 150 ml of ethanol, with stirring, the ethanol extracts and reaction solution are combined and concentrated, the solvent residues are stripped off under high vacuum and the residue is purified by column chromatography on 250 g of silica gel (63–200 μm) with cyclohexane/acetone (4:1).

Yield: 12.9–17.7 g (51–70% of theory) of a yellowish oil; mixture of diastereoisomers A and B in the ratio 4:1 Rf=0.36 for title compound of Example B.4. 0.12 for title compound A and B The crude product solidifies after prolonged standing. A diastereoisomerically pure sample of the main diastereoisomer A can be obtained by recrystallization from ether/petroleum ether.

$^1$H NMR (CDCl$_3$): (diastereoisomer A) δ=5.67–5.82 (m, 2H, H on C-4 and C-5); 3.50–3.77 (m, 4H, $H_a$ on C-7, $H_a$ on C-9 and hydroxymethyl-CH$_2$); 3.02 (dt, 1H, $H_b$ on C-9); 2.85 (m, 1H, $H_b$ on C-7); 2.2–2.4 (m, 3H); 1.87–2.00 (m, 3H); 1.62 (m, 1H, H on C-1); 1.46 ppm (s, 9H).

E.2. (1RS,2RS,6SR)-2-Hydroxymethyl-8-azabicyclo[4.3.0]non-4-ene

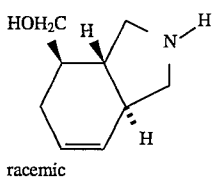
racemic 2.5 g (10 mmol) of title compound A of Example E.1. are placed in 10 ml of methanol. 10 ml of concentrated hydrochloric acid are run in rapidly and the mixture is stirred for 30 min. It is diluted to twice the volume with water, after which 45% sodium hydroxide solution is added dropwise, with stirring and ice-cooling, until the pH is ≧12. After concentration, the residue is extracted by boiling twice with ethanol, with stirring, the ethanol extracts are concentrated and the solvent residues are stripped off under high vacuum.

Yield: 2.1 g (product contains NaCl residues) Rf=0.20 Methylene chloride/methanol/17% aqueous ammonia (2:4:1)

$^1$H NMR (d$_6$-DMSO): δ=5.76 (d, 1H); 5.62 (d, 1H); 3.47–3.56 (m, 2H, $H_a$ on C-7 and $H_a$ on C-9); 3.32–3.47 (m, 1H, $H_a$ of hydroxymethyl-CH$_2$); 3.23–3.32 (m, 1H, $H_b$ of hydroxymethyl-CH$_2$); 2.77 (t, 1H, $H_b$ on C-9); 2.64 (t, 1H, $H_b$ on C-7); 2.10–2.24 (m, 2H, $H_a$ on C-3 and H on C-6); 1.77–1.88 (m, 1H, $H_b$ on C-3); 1.69 (m, 1H, H on C-2); 1.40 ppm (m, 1H, H on C-1).

Example F (1RS,2RS,6SR)-2-Ethoxycarbonylaminomethyl-8-azabicyclo[4.3.0]non-4-ene F.1. (1RS,2RS,6SR)-8-Tert-butoxycarbonyl-2-(4-toluenesulphonyloxymethyl)-8-azabicyclo[4.3.0]non-4-ene(diastereoisomer A) and
(1RS,2RS,6RS)-8-tert-butoxycarbonyl-2-(4-toluenesulphonyloxymethyl)-8-azabicyclo[4.3.0]non-4-ene(diastereoisomer B)

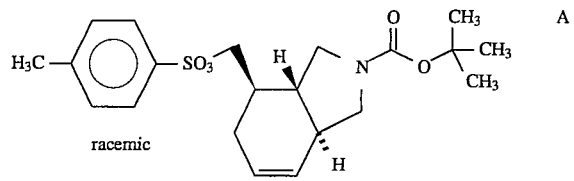
racemic A

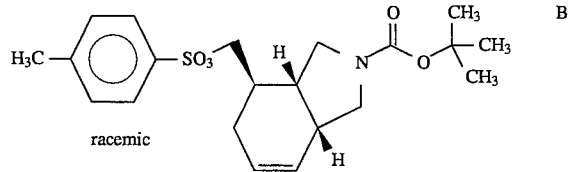
racemic B 12.7 g (0.05 mol) of the title compound of Example E.1. (crude mixture of diastereoisomers A and B) are placed in 25 ml of anhydrous pyridine and the mixture is cooled to −15° C. 11.0 g (0.0575 mol) of 4-toluenesulphonyl chloride are added in portions so that the internal temperature does not exceed −5° C. When the addition is complete, the mixture is stirred for 2 h at a temperature of −5° to −15° C. and then for 3 h at room temperature. 5 g of ice are added, the mixture is stirred for 5 min and added to 50 ml of water and the precipitate is filtered off with suction, washed with water and dried to constant weight at 50° C.

Yield: 14.4–16.3 g (71–80% of theory) pale pink solid mixture of diastereoisomers A and B A diastereoisomerically pure sample of the main diastereoisomer A can be obtained by recrystallization from methanol.

Melting point: 111°–113° C.

$^1$H NMR (CDCl$_3$): (diastereoisomer A) δ=7.79 (m, 2H, aryl-H); 7.36 (d, 2H, aryl-H); 5.74 and 5.78 (2d, 1H, H on C-5); 5.64 (m, 1H, H on C-4); 3.87–3.97 (m, 2H, tosyl-OCH$_2$—); 3.59 and 3.67 (2dd, 1H, H$_a$ on C-7); 3.48 (dd, 1H, H$_a$ on C-9); 2.78–2.96 (m, 2H, H$_b$ on C-7 and H$_b$ on C-9); 2.47 (s, 3H, aryl-CH$_3$); 2.22–2.36 (m, 2H, H$_a$ on C-3 and H on C-6); 2.06 (m, 1H, H on C-2); 1.80–1.98 (m, 1H, H$_b$ on C-3); 1.59 (m, 1H, H on C-1); 1.45 and 1.47 ppm (2s, 9H).

F.2. (1RS,2RS,6SR)-8-Tert-butoxycarbonyl-2-ethoxycarbonylaminomethyl-8-azabicyclo[4.3.0]non-4-ene(diastereoisomer A) and (1RS,2RS,6RS)-8-tert-butoxycarbonyl-2-ethoxycarbonylaminomethyl-8-azabicyclo[4.3.0]non-4-ene(diastereoisomer B)

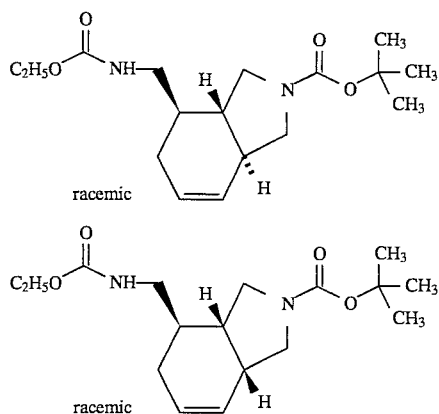

20.5 g (0.05 mol) of the title compound of Example F.1. (crude mixture of diastereoisomers A and B) and 6.5 g (0.1 mol) of sodium azide in 100 ml of DMF are heated at 70° C. for 4 h. The reaction solution is added to 200 ml of water and extracted once with 200 ml of petroleum ether and the petroleum ether phase is washed once with 50 ml of water, dried over sodium sulphate and concentrated at room temperature.

The residue is taken up with 80 ml of THF, and a solution of 13.1 g (0.05 mol) of triphenylphosphine in 80 ml of THF is added dropwise. When the addition is complete, the mixture is stirred for 20 h at room temperature, 150 ml of water are then slowly added dropwise and, when the addition is complete, the mixture is stirred for 15 min. Hydrochloric acid is added dropwise (concentrated HCl/water 1:3), with cooling, until the pH is 3–4, the THF is stripped off under vacuum at room temperature, the reaction solution is cooled to 0° C. and the precipitated triphenylphosphine oxide is filtered off with suction (or, if oily, taken up with MTBE).

The aqueous phase is adjusted to a pH of ≧12 by the addition of 10% sodium hydroxide solution and extracted with twice 100 ml of methylene chloride, the combined extracts are dried over sodium sulphate, 6.0 g (0.06 mol) of triethylamine are then added, a solution of 6.0 g (0.055 mol) of ethyl chloroformate in 20 ml of methylene chloride is added dropwise, with stirring, the mixture is stirred overnight at room temperature and the reaction solution is washed once with 100 ml of water, dried over sodium sulphate and concentrated.

The 23 g of crude product are purified by column chromatography on 100 g of silica gel (63–200 μm) with cyclohexane/acetone (4:1).

Yield: 12.4 g (76% of theory) of a viscous oil mixture of diastereoisomers A and B Rf values (cyclohexane/acetone 2:1): 0.32 for diastereoisomer A 0.29 for diastereoisomer B Diastereoisomers A and B are separated by column chromatography on 250 g of silica gel (35–70 μm) with cyclohexane/acetone (8:1).

Yield: 4.3 g (26% of theory) of diastereoisomer A (viscous oil) 2.4 g (15% of theory) of mixed fraction 0.6 g (4% of theory) of diastereoisomer B $^1$H NMR (Cl$_2$DC-CDCl$_2$; 80° C.): Diastereoisomer A: δ=5.75 (d, 1H, H on C-5); 5.66 (m, 1H, H on C-4); 4.67 (br, 1H, NH); 4.08 (q, 2H, ethoxy-CH$_2$); 3.62 (br, 2H, H$_a$ on C-7 and H$_a$ on C-9); 3.19 (br, 1H, H$_a$ on CH$_2$—NH); 3.05 (br, H$_b$ on CH$_2$—NH); 2.96 (dd, 1H, H$_b$ on C-9); 2.81 (dd, 1H, H$_b$ on C-7); 2.24–2.34 (m, 2H, H$_a$ on C-3 and H on C-6); 1.78–1.94 (m, 2H, H on C-2 and H$_b$ on C-3); 1.54 (m, 1H, H on C-1); 1.43 (s, 9H); 1.22 ppm (t, 3H, ethoxy-CH$_3$).

Diastereoisomer B: δ=5.69 (m, 1H, H on C-4); 5.57 (m, 1H, H on C-5); 4.65 (br, 1H, NH); 4.08 (q, 2H, ethoxy-CH$_2$); 3.52 (dd, 1H, H$_a$ on C-7); 3.41 (dd, 1H, H$_a$ on C-9); 3.29 (dd, 1H, H$_b$ on C-9); 3.24 (dd, 1H, H$_a$ on CH$_2$—NH); 3.03–3.12 (m, 2H, H$_b$ on C-7 and H$_b$ on CH$_2$—NH); 2.68 (m, 1H, H on C-6); 2.12–2.22 (m, 2H, H on C-1 and H$_a$ on C-3); 1.74–1.87 (m, 2H, H on C-2 and H$_b$ on C-3); 1.43 (s, 9H); 1.22 ppm (t, 3H, ethoxy-CH$_3$).

F.3. (1RS,2RS,6SR)-2-Ethoxylcarbonylaminomethyl-8-azabicyclo[4.3.0]non-4-ene

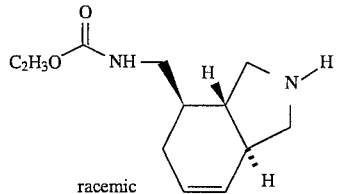

1.6 g (5.7 mmol) of title compound A of Example F.2. are placed in 10 ml of methanol. 8 ml of concentrated hydrochloric acid are run in rapidly and the mixture is stirred for 30 min. It is diluted to twice the volume with water, after which 45% sodium hydroxide solution is added dropwise, with stirring and ice-cooling, until the pH is ≧12. The mixture is extracted four times with methylene chloride, the combined organic phases are dried over sodium sulphate and concentrated and the solvent residues are stripped off under high vacuum.

Yield: 0.8 g (63% of theory) of a viscous oil Rf=0.16 Methylene chloride/methanol/17% aqueous ammonia (15:4:0.5)

$^1$H NMR (CDCl$_3$): δ=5.81 (d, 1H, H on C-5); 5.67 (m, 1H, H on C-4); 5.00 (br, 1H, NH); 4.10 (q, 2H, ethoxy-CH$_2$); 3.18–3.28 and 3.08 (m, 3H and m, 1H: H$_a$ on C-7, H$_a$ on C-9, H$_a$ and H$_b$ on CH$_2$—NH—CO); 2.67 (dd, 1H, H$_b$ on C-9); 2.53 (dd, 1H, H$_b$ on C-7); 2.34 (m, 1H, H$_a$ on C-3); 2.25 (m, 1H, H on C-6); 1.79–1.96 (m, 2H, H on C-2 and H$_b$ on C-3); 1.50 (m, 1H, H on C-1); 1.24 ppm (t, 3H, ethoxy-CH$_3$).

Example G (1RS,2SR,6RS)-2-Hydroxymethyl-8-azabicyclo[4.3.0]non-4-ene

G.1. (E)-1-Tert-butoxycarbonylamino-2,4-pentadiene

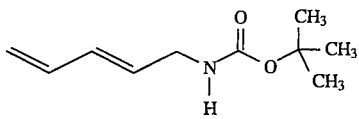

8.3 g (0.1 mol) of (E)-1-amino-2,4-pentadiene (title compound of Example B.2.) are placed in 50 ml of MTBE, and 20 mg of 4-hydroxyanisole are added. A solution of 22.9 g (0.105 mol) of di-tert-butyl dicarbonate in 50 ml of MTBE is then added dropwise at an internal temperature of 20°–30° C. When the addition is complete, the mixture is stirred for 20 h at room temperature. After concentration, the di-tert-butyl dicarbonate residues are stripped off under high vacuum at 40° C.

Yield: 18.9 g (crude product) of a colourless oil Rf=0.25 Cyclohexane/acetone (4:1)

$^1$H NMR (CDCl$_3$): δ=6.05–6.43 (m, 2H, H on C-3 and C-4); 5.68 (dd, 1H, H on C-2, J=14 and 6 Hz); 5.17 (dd, 1H, H$_a$ on C-5, J=16 Hz); 5.07 (dd, 1H, H$_b$ on C-5, J=10 Hz); 4.75 (br, 1H, NH); 3.77 (t, 2H, H on C-1); 1.45 ppm (s, 9H).

G.2. (1RS,2RS,6RS)-2-Tert-butoxycarbonylaminomethyl-7,9-dioxo-8-oxabicyclo[4.3.0]non-3-ene

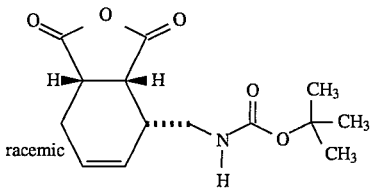

83.2 g (1.0 mol) of (E)-1-amino-2,4-pentadiene (title compound of Example B.2.) are placed in 250 ml of PETBE, and 0.1 g of 4-hydroxyanisole is added. A solution of 229.2 g (1.05 mol) of di-tert-butyl dicarbonate in 250 ml of MTBE is then added dropwise at an internal temperature of 20°–30° C. When the addition is complete, the reaction mixture is stirred for 20 h at room temperature. It is concentrated and taken up with 1 l of toluene. 103.0 g (1.05 mol) of maleic anhydride are added and the mixture is stirred for 24 h at an internal temperature of 60° C. The precipitate is filtered off with suction, washed with toluene and dried to constant weight at 50° C.

Yield: 208.2 g (74% of theory) white crystalline solid
Melting point: 157°–159° C.

$^1$H NMR (d6-DMSO): δ=5.81 (m, 1H, H on C-4); 5.59 (d, 1H, H on C-3); 3.77 (dd, 1H, H$_a$ on CH$_2$—NH); 3.44 (m, 2H, H on C-1 and H$_b$ on CH$_2$—NH); 2.94 (m, 1H, H on C-2); 2.66 (m, 1H, H on C-6); 2.16 (m, 1H, H$_a$ on C-5); 2.06 (m, 1H, H$_b$ on C-5); 1.43 ppm (s, 9H).

G.3. Methyl (1RS,2SR,6RS)-9-oxo-8-azabicyclo[4.3.0]non-4-ene-2-carboxylate

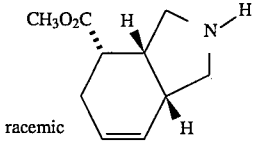

83.2 g (1.0 mol) of (E)-1-amino-2,4-pentadiene (title compound of Example B.2.) are placed in 250 ml of THF, and 0.1 g of 4-hydroxyanisole is added. A solution of 229.2 g (1.05 mol) of di-tert-butyl dicarbonate in 250 ml of THF is then added dropwise at an internal temperature of 20°–30° C. When the addition is complete, the mixture is stirred for 20 h at room temperature. 103.0 g (1.05 mol) of maleic anhydride are added and the mixture is refluxed for 5 h. After concentration, the residue is taken up with 500 ml of methanol, 30 ml of p-toluene-sulphonic acid are added and the mixture is then refluxed for a further 5 h. After ice-cooling and stirring, a solution of 20 g of sodium carbonate in 500 ml of water is rapidly added dropwise, the reaction mixture is left to stand in the ice bath for a further 30 min and the precipitate is filtered off with suction, washed with a small volume of water and dried to constant weight at 50° C.

Yield: 125–148 g (64–76% of theory) white crystalline solid

Melting point: 190°–193° C.

$^1$H NMR (d$_6$-DMSO): δ=7.50 (s, 1H, NH); 5.77 (m, 1H, H on C-4); 5.56 (m, 1H, H on C-5); 3.60 (s, 3H, CH$_3$O); 3.42 (dd, 1H, H$_a$ on C-7); 3.16 (dd, 1H, H on C-1); 3.00 (m, 1H, H on C-6); 2.88 (dd, 1H, H$_b$ on C-7); 2.67 (m, 1H, H on C-2); 2.02–2.18 ppm (m, 2H, H$_a$ and H$_b$ on C-3).

G.4. (1RS,2SR,6RS)-2-Hydroxymethyl-8-azabicyclo[4.3.0]non-4-ene

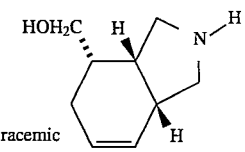

19.6 g (0.1 mol) of the title compound of Example G.3. are placed in 100 ml of THF under an inert gas atmosphere (suspension). 100 ml (0.15 mol) of a 1.5M solution of DIBAH in toluene are added dropwise at an internal temperature of 10°–20° C. The resulting clear, homogeneous solution is added dropwise to a suspension of 1.9 g of lithium alanate in 50 ml of THF. When the addition is complete, the mixture is stirred for 15 min at room temperature and then for 30 min at the reflux temperature. After cooling, 3.8 g (0.1 mol) of lithium alanate are added in portions and the mixture is then refluxed for 24 h. After cooling, 50 ml of water and 10 ml of 1M sodium hydroxide solution are successively added dropwise and the precipitate is filtered off with suction and extracted by boiling with three times 150 ml of ethanol. The filtrate and extracts are combined and concentrated.

Yield: 16.4 g (product contains lithium hydroxide and aluminium hydroxide) Rf=0.3 Methylene chloride/methanol/17% aqueous ammonia (2:4:1)

Example H (1RS,2SR,6RS)-2-Ethoxycarbonylamimomethyl-8-azabicyclo[4.3.0]non-4-ene H.1. (1RS,2SR,6RS)-8-Tert-butoxycarbonyl-2-hydroxymethyl-8-azabicyclo[4.3.0]non-4-ene

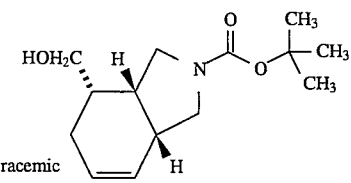

16.4 g of the crude product of Example G.4. (corresponds to 0.1 mol of the title compound of Example G.4.) are dissolved in 100 ml of THF. A solution of 22.9 g (0.105 mol) of di-tert-butyl dicarbonate in 100 ml of THF is added dropwise at an internal temperature of 0°–5° C. and the mixture is stirred for 24 h at 0° C. and then for a further 24 h at room temperature. After concentration, the crude product is purified by column chromatography on 250 g of silica gel (63–200 μm) with cyclohexane/acetone (2:1).

Yield: 13.7 g (54% of theory over 2 stages); viscous oil Rf=0.21 for title compound 0.08 for title compound of Example G.4.

H.2. (1RS,2SR,6RS)-8-Tert-butoxycarbonyl-2-(4-toluenesulphonyloxymethyl)-8-azabicyclo[4.3.0]non-4-ene

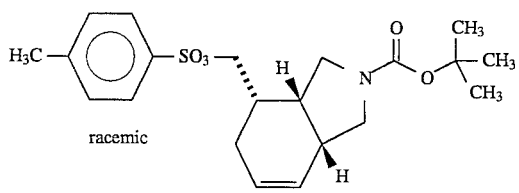

The title compound is obtained analogously to Example F.1. from the title compound of Example H.1.

Yield: 81–83% of theory

Melting point: 160°–162° C.

$^1$H NMR (CDCl$_3$): δ=7.79 (m, 2H, aryl-H); 7.37 (d, 2H, aryl-H); 5.67 (m, 1H, H on C-4); 5.47 (m, 1H, H on C-5); 3.78–3.97 (m, 2H, tosyl-OCH$_2$—); 3.13–3.42 (m, 3H, CH$_2$—N); 2.95 (t, 1H, CH$_2$—N); 2.74 (m, 1H); 2.54 (m, 1H); 2.47 (s, 3H, aryl-CH$_3$); 2.32 (m, 1H, H on C-2); 2.06 (m, 1H, H$_a$ on C-3); 1.66–1.83 (m, 1H, H$_b$ on C-3); 1.44 ppm (s, 9H).

H.3. (1RS,2SR,6RS)-8-Tert-butoxycarbonyl-2-ethoxycarbonylaminomethyl-8-azabicyclo[4.3.0]non-4-ene

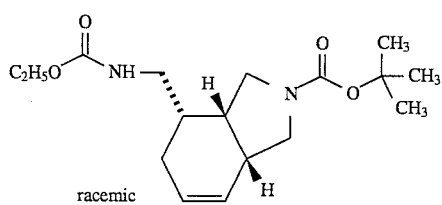

The title compound is obtained analogously to Example F.2. from the title compound of Example H.2.

The crude product is purified by column chromatography on silica gel (63–200 μm) with cyclohexane/acetone (2:1).

Yield: 76% of theory; clear viscous oil Rf=0.35 (cyclohexane/acetone 2:1)

$^1$H NMR (Cl$_2$DC-CDCl$_2$; 80° C.): δ=5.69 (m, 1H, H on C-4); 5.47 (d, 1H, H on C-5); 4.59 (br, 1H, NH); 4.10 (q, 2H, ethoxy-CH$_2$); 3.38 (dd, 1H); 3.32 (m, 1H); 3.24 (m, 1H); 3.01–3.08 (m, 3H); 2.79 (m, 1H); 2.47 (m, 1H); 2.07 (m, 2H); 1.78 (m, 1H); 1.42 (s, 9H); 1.22 ppm (t, 3H, ethoxy-CH$_3$).

H.4. (1RS,2SR,6RS)-2-Ethoxycarbonylaminomethyl-8-azabicyclo[4.3.0]non-4-ene

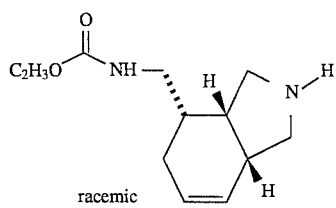

The title compound is obtained analogously to Example C.3. from the title compound of Example H.3.

Yield: 42% of theory Rf=0.93 for title compound of Example H.3. 0.23 for title compound Methylene chloride/methanol/17% aqueous ammonia (15:4:0.5)

Example I (1SR,2RS,3RS,6SR)-2-Ethoxycarbonylamino-3-methyl-8-azabicyclo[4.3.0]non-4-ene I.1. N-[(2E,4E)-2,4-Hexadienyl]-phthalamide

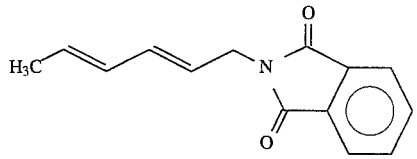

The title compound is obtained analogously to Example B.1. from (2E,4E)-1-bromo-2,4-hexadiene.

Yield: 77–79% of theory

Melting point: 114°–117° C. (sample recrystallized from ethanol)

$^1$H NMR (CDCl$_3$): δ=7.85 (m, 2H); 7.72 (m, 2H); 6.25 (dd, 1H); 6.00 (ddd, 1H); 5.5–5.8 (m, 2H); 4.29 (d, 2H); 1.74 ppm (d, 3H).

I.2. (2E,4E)-1-Amino-2,4-hexadiene

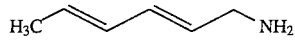

The title compound is obtained analogously to Example B.2. from the title compound of Example I.1.; boiling range: 40°–70° C. at 16–18 mbar.

Yield: 67–83% of theory

I.3. Ethyl (E)-4-[(2E,4E)-2,4-hexadienylamino]-2-butenoate

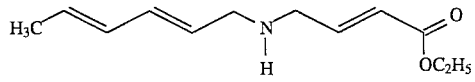

The title compound is obtained analogously to Example B.3. from the title compound of Example I.2.

Yield: 46% of theory $^1$H NMR (CDCl$_3$): δ=6.98 (dt, 1H); 5.9–6.25 (m, 3H); 5.5–5.8 (m, 2H); 4.19 (q, 2H); 3.40 (dd, 2H); 3.27 (d, 2H); 1.76 (d, 3H); 1.29 ppm (t, 3H).

I.4. Ethyl (1RS,2RS,3RS,6SR)-8-tert-butoxycarbonyl-3-methyl-8-azabicyclo[4.3.0]non-4-ene-2-carboxylate (diastereoisomer A) and ethyl (1RS,2RS,3SR,6RS)-8-tert-butoxycarbonyl-3-methyl-8-azabicyclo[4.3.0]non-4-ene-2-carboxylate (diastereoisomer B)

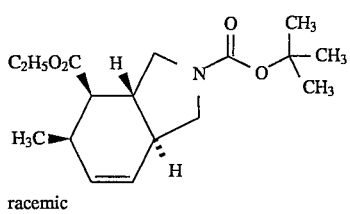

racemic

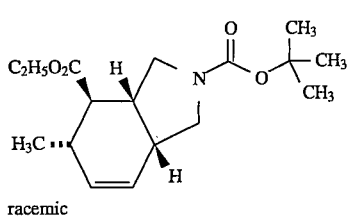

racemic

The title compounds are obtained analogously to Example B.4. from the title compound of Example I.3.

Yield: 70% of theory; mixture of 2 diastereoisomers A and B in the ratio A:B=4:1 Rf=0.49 (cyclohexane/acetone 2:1)

I.5. (1RS,2RS,3RS,6SR)-8-Tert-butoxycarbonyl-3-methyl-8-azabicyclo[4.3.0.]non-4-ene-2-carboxylic acid

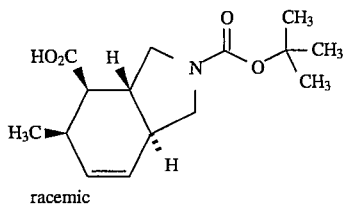

racemic

The starting material is a solution of 1.17 g (21 mmol) of potassium hydroxide in 20 ml of water. A solution of 5.9 g (19 mmol) of the title compound of Example I.4. in 20 ml of methanol is added and the mixture is refluxed for 48 h under a nitrogen atmosphere. After concentration, it is taken up with water and extracted once with methylene chloride, the aqueous phase is adjusted to pH 3–4 with acetic acid and the precipitate is filtered off with suction, washed with water, dried at room temperature and recrystallized from cyclohexane/acetone 6:1.

Yield: 2.25 g (42% of theory)
Melting point: 189° C.
$^1$H NMR (d$_6$-DMSO): δ=5.77 (d, 1H); 5.61 (m, 1H); 3.67 (m, 1H); 3.54 (m, 1H); 2.61–2.95 (m, 4H); 2.30 (m, 1H); 1.82 (m, 1H); 1.40 (s, 9H); 0.90 ppm (d, 3H).

I.6. (1SR,2RS,3RS,6SR)-8-Tert-butoxycarbonyl-2-ethoxycarbonylamino-3-methyl-8-azabicyclo[4.3.0]non-4-ene

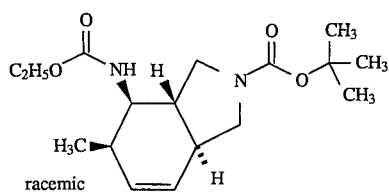

racemic

The title compound is obtained analogously to Example C.2. from 2.25 g (8 mmol) of the title compound of Example I.5. Changes compared with Example C.2.: reflux in ethanol for 8 h instead of 4 h; purification by column chromatography on 100 g of silica gel (63–200 μm) with toluene/ethyl acetate (2:1).

Yield: 1.6 g (59% of theory) of a clear oil
$^1$H NMR (CDCl$_3$): δ=5.68 and 5.72 (2d, 1H); 5.61 (m, 1H); 4.81 (m, 1H); 4.0–4.2 (m, 3H); 3.53 (m), 3.62 (m) and 3.72 (dd) [2H]; 3.08 (t, 1H); 2.92 (t, 1H); 2.75 (m, 1H); 2.47 (m, 1H); 1.83 (m, 1H); 1.47 (m, 9H); 1.25 (m, 3H); 0.97 ppm (d, 3H).

I.7. (1SR,2RS,3RS, 6SR)-2-Ethoxycarbonylamino-3-methyl-8-azabicyclo[4.3.0]non-4-ene

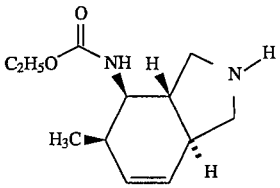

racemic

The title compound is obtained analogously to Example C.3. from 1.6 g (4.7 mmol) of the title compound of Example I.6.

Yield: 0.7 g (70% of theory) of a yellowish oil Rf=0.09 Methylene chloride/methanol/17% aqueous ammonia (15:4:0.5)

Example K (1RS,2RS,6RS)-2-Ethoxycarbonylaminomethyl-8-azabicyclo[4.3.0]non-4-ene K1. Diethyl 3-phthalimidomethyl-cyclohex-4-ene-1,2-dicarboxylate

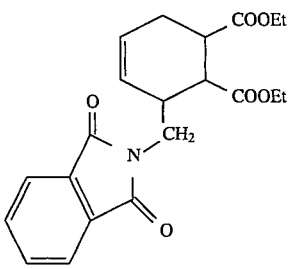

10.67 g (50 mmol) of N-[(E)-2,4-pentadienyl]-phthalimide (title compound of Example B.1.) and 8.61 g of diethyl fumarate are refluxed for 2 days in 50 ml of toluene. The reaction mixture is concentrated and the residue is chromatographed on silica gel (eluent: cyclohexane/acetone 8:1).

Yield: 14.8 g (77% of theory)
Melting point: 80°–84° C.

K.2. Ethyl (1RS,2RS,6RS)-9-oxo-8-azabicyclo[4.3.0]non-4-ene-2-carboxylate (A) and ethyl (1RS,2RS,6SR)-9-oxo-8-azabicyclo[4.3.0]non-4-ene-2-carboxylate (B)

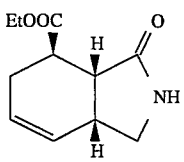

racemic

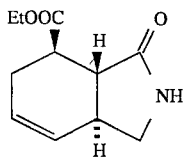

racemic 150.3 g (0.39 mol) of the title compound of Example K.1. are placed in 720 ml of ethanol, and 173.3 g (2.9 mol) of ethylenediamine are added dropwise, with ice-cooling. The mixture is stirred for 20 h at room temperature, concentrated under vacuum, diluted with water (ca. 700 ml), adjusted to pH 2–3 with concentrated hydrochloric acid and extracted with three times 500 ml of dichloromethane. The organic phase is dried (sodium sulphate) and concentrated under vacuum. The diastereoisomers are resolved by chromatography (eluent: cyclohexane/acetone 1:1).

Yield: 36.7 g of product A (45% of theory) RF=0.47 (cyclohexane/acetone 1:1) 27.0 g of product B (45% of theory) RF=0.22 (cyclohexane/acetone 1:1)

K.3. (1RS,2RS,6RS)-2-Hydroxymethyl-8-azabicyclo[4.3.0]non-4-ene

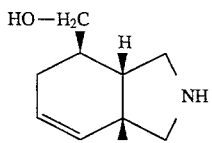

racemic 5.2 g (25 mmol) of ethyl (1RS,2RS,6RS)-9-oxo-8-azabicyclo[4.3.0]non-4-ene-2-carboxylate (product A of Example K.2.) are dissolved in 50 ml of tetrahydrofuran under a nitrogen atmosphere, and 130 ml of a 1.5 molar solution of di(isobutyl)aluminium hydride (195 mmol) are then added dropwise. The solution is refluxed for 16 h. When the reaction is complete, 60 ml of methanol, 30 ml of tert-butyl methyl ether and 10 ml of water are successively added dropwise and the mixture is filtered with suction, Tonsil being added. The residue on the suction filter is stirred twice with an ethanol/concentrated ammonia/water mixture (10:1:1) and again filtered off with suction. The combined filtrates are concentrated and the crude product is purified by chromatography (eluent: dichloromethane/methanol/concentrated ammonia 2:4:1).

Yield: 2.7 g (71% of theory)

$^1$H NMR (DMSO-d$_6$): 5.69 (m, 1H, 4-H); 5.60 (m, 1H, 5-H); 3.39 (dd, 1H, 10a-H); 3.26 (dd, 1H, 10b-H); 2.97 (m, 2H, 7a-H, 9a-H), 2.63 (m, 1H, 9b-H); 2.38 (bs, 1H, 6-H)M; 2.32 (dd, 1H, 7b-H); 2.06 (m, 1H, 3a-H); 1.95 (m, 1H, 1-H); 1.77 (m, 1H, 3b-H); 1.44 ppm (m, 1H, 2-H).

K.4. (1RS,2RS,6RS)-8-Tert-butoxycarbonyl-2-hydroxymethyl-8-azabicyclo[4.3.0]non-4-ene

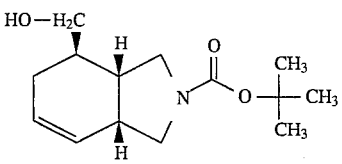

racemic

The product of Example K.3. (8.87 g; 58 mmol) is reacted as described in Example H.1.

Yield: 11.0 g (75% of theory) RF=0.25 (cyclohexane/acetone 2:1)

K.5. (1RS,2RS,6RS)-8-Tert-butoxycarbonyl-2-(4-toluenesulphonyloxymethyl)-8-azabicyclo[4.3.0]non-4-ene

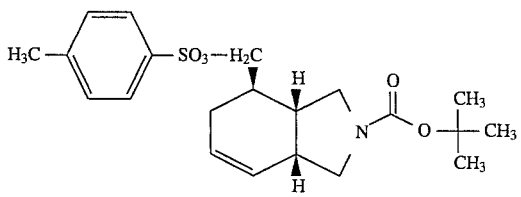

racemic

The title compound is obtained analogously to Example F.1. from the product of Example K.4.

Yield: 97% of theory RF=0.40 (cyclohexane/acetone 2:1)

K.6. (1RS,2RS,6RS)-8-Tert-butoxycarbonyl-2-azidomethyl-8-azabicyclo[4.3.0]non-4-ene

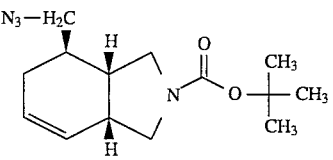

racemic

A solution of 33 g (0.08 mol) of (1RS,2RS,6RS)-8-tert-butoxycarbonyl-2-(4-toluenesulphonyloxymethyl)-8-azabicyclo[4.3.0]non-4-ene (title compound of Example K.5.) and 15.8 g (0.24 mol) of sodium azide in 200 ml of N,N-dimethylformamide is stirred for 40 h at 70° C. The cooled solution is diluted with water (500 ml) and extracted with three times 250 ml of petroleum ether. The combined organic phase is washed with 5% sodium hydrogen carbonate solution, dried (sodium sulphate) and concentrated.

Yield: 21.6 g (97%)

$^1$H NMR (CDCl$_3$): 5.71 (m, 1H, C═CH); 5.58 (m, 1H, C═CH); 3.61–3.22 (m, 2H); 3.10 (m, 1H); 2.70 (bs, 1H); 2.24 (m, 2H); 1.91 (m, 2H); 1.47 ppm (s, 9H, tert-butyl).

K.7. (1RS,2RS,6RS)-8-Tert-butoxycarbonyl-2-aminomethyl-8-azabicyclo[4.3.0]non-4-ene

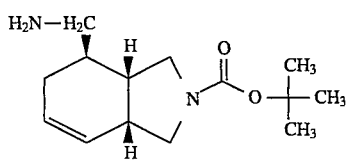

racemic

A solution of the azido compound of Example K.6.(21.6 g; 78 mmol) in 150 ml of pyridine/water (5:1) is saturated with hydrogen sulphide, with ice-cooling, and then left to stand for 20 h at room temperature. When the reaction is complete, the mixture is concentrated under vacuum and distilled several times with toluene and the residue is chromatographed (eluent: cyclohexane/acetone 1:1).

Yield: 11.0 g (66% of theory) RF=0.12 (cyclohexane/acetone 1:1)

K.8. (1RS,2RS,6RS)-8-Tert-butoxycarbonyl-2-(ethoxycarbonylaminomethyl)-8-azabicyclo[4.3.0]non-4-ene

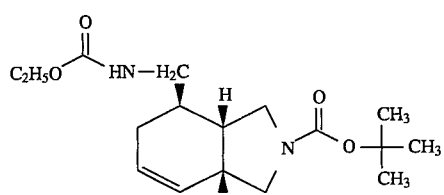

racemic 3.7 g (15 mmol) of (1RS,2RS,6RS)-8-tert-butoxycarbonyl-2-aminomethyl-8-azabicyclo[4.3.0]non-4-ene are placed in 40 ml of dioxane and 15 ml of water, 2.3 g (16 mmol) of potassium carbonate are added and 1.75 g (16 mmol) of ethyl chloroformate are added dropwise at room temperature. After stirring for two hours, the mixture is concentrated under vacuum and the residue is taken up with dichloromethane (70 ml), extracted by shaking with twice 25 ml of water, dried (sodium sulphate) and concentrated. The crude product is purified by chromatography (cyclohexane/acetone 2:1).

Yield: 2.8 g (59% of theory) RF=0.53 (cyclohexane/acetone 1:1)

K.9. (1RS,2RS,6RS)-2-(Ethoxycarbonylaminomethyl)-8-azabicyclo[4.3.0]non-4-ene

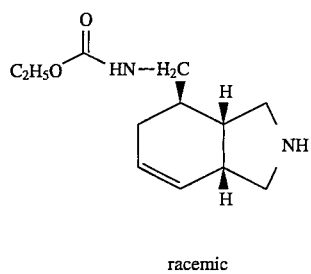

racemic 7.6 g (23 mmol) of the product of Example K.8. are placed in 100 ml of methanol/water (1:1), and 30 ml of semi-concentrated hydrochloric acid are run in at room temperature. When the evolution of gas has ceased, the mixture is stirred for 30 minutes, diluted with ice-water (ca. 100 ml) and adjusted to pH 12 with concentrated sodium hydroxide solution. The aqueous phase is extracted with four times 100 ml of dichloromethane. The extracts are combined, dried over sodium sulphate and concentrated under vacuum.

Yield: 3.9 g (76% of theory) RF=0.45 (dichloromethane/methanol/concentrated ammonia (2:4:0.1)

Example L (1RS,2RS,6RS)-2-Aminomethyl-8-azabicyclo[4.3.0]non-4-ene bis-trifluoromethanesulphonate

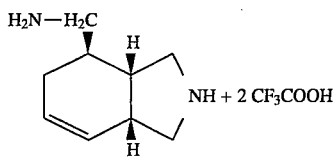

racemic 30 ml of trifluoroacetic acid are added to a solution of 2.0 g (8 mmol) of (1RS,2RS,6RS)-8-tert-butoxycarbonyl-2-aminomethyl-8-azabicyclo[4.3.0]non-4-ene (product of Example K.7.) in 30 ml of dichloromethane and the mixture is left to stand for 30 minutes at room temperature. The solvent and the acid are distilled off in the presence of toluene and the residue is distilled several times with toluene. The product is dried in a vacuum desiccator over potassium hydroxide/phosphorus pentoxide (1:1).

Yield: 1.5 g of a brown oil $^1$H NMR (DMSO-$d_6$): 5.78 (m, 1H, C=CH); 5.60 (m, 1H, C=CH); 3.34 (M, 2H); 3.03 (m, 1H), 2.87 (m, 2H), 2.73 (m, 1H); 2.45 (m, 1H); 2.34 (m, 1H); 2.22 (M, 1H); 1.94 ppm (m, 2H). FAB-MS: M+1=153.

Example M (1RS,2RS,6RS)-2-Ethoxycarbonylaminomethyl-8-azabicyclo[4.3.0]non-4-ene (The product is identical to the title compound of Example F.)

M.1. (1RS,2RS,6SR)-2-Hydroxymethyl-8-azabicyclo[4.3.0]non-4-ene

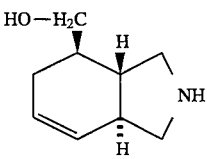

racemic

Ethyl (1RS,2RS,6RS)-9-oxo-8-azabicyclo[4.3.0]non-4-ene-2-carboxylate (product B of Example K.2.) is reacted analogously to Example K.3.

Yield: 75% of theory RF=0.22 (dichloromethane/methanol/concentrated ammonia (15:4:0.5)

M.2. (1RS,2RS,6SR)-8-Tert-butoxycarbonyl-2-hydroxymethyl-8-azabicyclo[4.3.0]non-4-ene

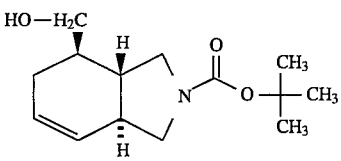

racemic

The product of Example M.1. is reacted analogously to Example K.4.

Yield: 64% of theory
RF=0.23 (cyclohexane/acetone 2:1)

M.3. (1RS,2RS,6SR)-8-Tert-butoxycarbonyl-2-(4-toluene-sulphonyloxymethyl)-8-azabicyclo[4.3.0]non-4-ene

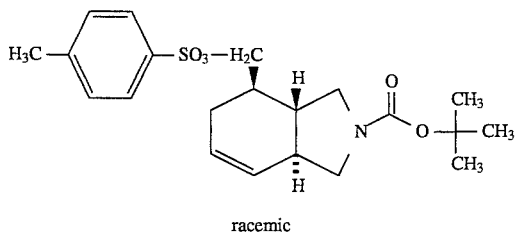

racemic

The title compound is obtained analogously to Example F.1. from the product of Example M.2.

Yield: 91–98% of theory RF=0.59 (cyclohexane/acetone 2:1)

M.4. (1RS,2RS,6SR)-8-Tert-butoxycarbonyl-2-azidomethyl-8-azabicyclo[4.3.0]non-4-ene

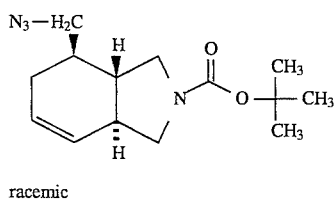

racemic 4.15 g (64 mmol) of sodium azide are added to a solution of 13.0 g (32 mmol) of the product of Example M.3. in 80 ml of N,N-dimethylformamide and the mixture is stirred for 4 h at 70° C. The same amount of sodium azide is then added again and the mixture is stirred for a further 6 h at 100° C. It is then worked up as described in Example Yield: 7.0 g (79% of theory) RF=0.55 (cyclohexane/acetone 2:1)

M.5. (1RS,2RS,6SR)-8-Tert-butoxycarbonyl-2-aminomethyl-8-azabicyclo[4.3.0]non-4-ene

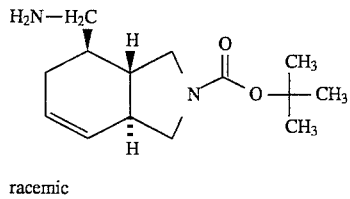

racemic

The azido compound of Example M.4. is reacted as described in Example K.7.

Chromatography is carried out with methanol/dichloromethane/concentrated ammonia (15:2:0.1).

Yield: 75% of theory RF=0.12 (methanol/dichloromethane/concentrated ammonia (15:2:0.1)

M.6. (1RS,2RS,6SR)-8-Tert-butoxycarbonyl-2-(ethoxycarbonylmethyl)-8-azabicyclo[4.3.0]non-4-ene

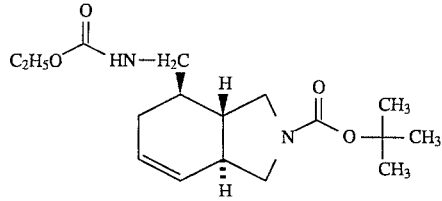

racemic 4.3 g (17 mmol) of the amino compound of Example M.5. and 1.9 g (19 mmol) of triethylamine are placed in 50 ml of dichloromethane, a solution of 2.2 g (20 mmol) of ethyl chloroformate in 10 ml of dichloromethane is added dropwise at 0° C. and the mixture is stirred for 24 h at room temperature. Water (50 ml) is added to the solution and the phases are separated. The aqueous phase is reextracted with three times 40 ml of dichloromethane. The organic phases are combined, dried (sodium sulphate) and concentrated.

Yield: 5.3 g (96% of theory)

$^1$H NMR (CDCl$_2$—CDCl$_2$, 80° C.): 5.79 (ddd, 1H, C=CH); 5.58 (m, 1H, C=CH); 4.61 (bs, 1H, carbamate-NH); 4.23 (m, 1H); 4.12 (q, 2H, ethyl-CH$_2$); 3.99 (m, 1H); 3.20–3.08 (m, 2H); 2.82 (m, 2H); 2.25 (m, 2H); 2.09 (m, 1H); 1.84 (m, 2H); 1.42 (s, 9H, tert-butyl); 1.37 ppm (t, 3H, ethyl-CH$_3$).

M.7. (1RS,2RS,6SR)-2-(Ethoxycarbonylaminomethyl)-8-azabicyclo[4.3.0.]non-4-ene (1RS,2RS,6SR)-8-Tert-butoxycarbonyl-2-(ethoxycarbonylaminomethyl)-8-azabicyclo[4.3.0]non-4-ene is reacted as described in Example K.9.

Yield: quantitative RF=0.55 (methanol/dichloromethane/concentrated ammonia 15:4:0.5)

Example N (1SR,2RS,6RS)-2-Methylamino-8-azabicyclo[4.3.0]non-ene

N.1. (1RS,2RS,6RS)-9-Oxo-azabicyclo[4.3.0]non-4-ene-2-carboxylic acid

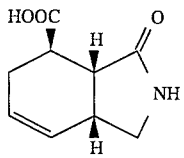

racemic 8.36 g (40 mmol) of ethyl (1RS,2RS,6RS)-9-oxo-8-azabicyclo[4.3.0]non-4-ene-2-carboxylate (product A of Example K.2.) are stirred with 30 ml of water and 5 ml of concentrated sulphuric acid for 40 h at 60° C. The product precipitates out on cooling. The precipitate is washed with a small volume of cold water and dried in a vacuum drying cabinet at 50° C.

Yield: 4.80 g (66% of theory)

$^1$H NMR (DMSO-d$_6$): 12.35 (s, 1H, COOH); 7.60 (s, 1H, lactam-NH); 5.74 (m, 1H, C=CH); 5.59 (m, 1H, C=CH); 3.45 (dd, 1H, 7a-H); 2.95–2.85 (m, 4H, 1-H, 2-H, 6-H, 7b-H); 2.29 (m, 1H, 3a-H); 2.00 ppm (m, 1H, 3b-H).

N.2. (1SR,2RS,6RS)-2-Ethoxycarbonylamino-9-oxo-8-azabicyclo[4.3.0]non-4-ene

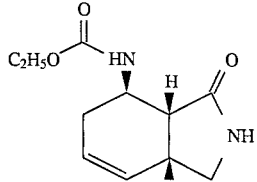

racemic (1RS,2RS,6RS)-9-oxo-8-azabicyclo[4.3.0]non-4-ene-2-carboxylic acid (title compound of Example N.1.) is reacted analogously to Example C.2.

Yield: 68% of theory RF=0.06 (cyclohexane/acetone 1:1)
N.3. (1SR,2RS,6RS)-2-Methylamino-8-azabicyclo[4.3.0]-non-4-ene

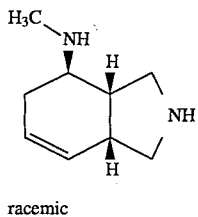

racemic

The title compound is obtained by reacting the product of Example N.2. with 10 equivalents of di(isobutyl)aluminium hydride analogously to Example K.3. and working up the reaction product.

Yield: 51% of theory $^1$H NMR (CDCl$_3$): 5.72 (m, 1H, C=CH); 5.68 (m, 1H, C=CH); 3.19–3.10 (m, 2H); 2.88 (dd, 1H); 2.60 (dd, 1H); 2.50 (m, 1H); 2.44 (s, 3H, N—CH$_3$); 2.33–2.28 (m, 2H); 2.19 (m, 1H); 1.89 ppm (m, 1H).

Example O (1SR,2SR,6RS)-2-Methylamino-8-azabicyclo[4.3.0]non-4-ene

O.1. (1RS,2SR,6RS)-9-Oxo-8-azabicyclo[4.3.0]non-4-ene-2-carboxylic acid

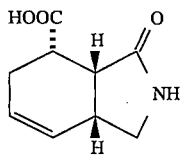

racemic

The starting materials are 0.2 g of concentrated sulphuric acid, 25 ml of water and 25 ml of acetic acid at 60° C. 9.8 g (50mmol) of the product of Example G.3. are added in small portions. The mixture is stirred for 5 h at 60° C. For working-up, a solution of 0.8 g of sodium hydrogen carbonate in 10 ml of water is added and the mixture is concentrated under vacuum. The residue is suspended in 40 ml of water and dissolved by the addition of concentrated sodium hydroxide solution, with ice-cooling. After the insoluble constituents have been filtered off with suction, the filtrate is acidified with semiconcentrated hydrochloric acid and cooled to 0° C. again. The product which precipitates out is washed with a small volume of cold water and then dried in a vacuum drying cabinet at 50° C.

Yield: 4.8 g (53% of theory)
Melting point: 192°–193° C.

O.2. (1SR,2SR,6RS)-2-Ethoxycarbonylamino-9-oxo-8-azabicyclo[4.3.0]non-4-ene

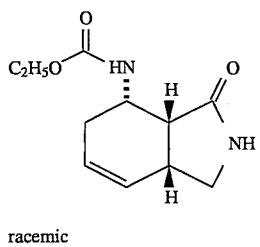

racemic (1RS,2SR,6RS)-9-Oxo-8-azabicyclo[4.3.0]non-4-ene-2-carboxylic acid (title compound of Example O.1.) is reacted as described in Example C.2.

Yield: 68% of theory
Melting point: 160°–164° C.

O.3. (1SR,2SR,6RS)-2-Methylamino-8-azabicyclo[4.3.0] non-4-ene

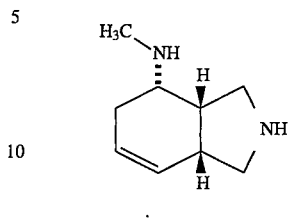

racemic

The title compound is obtained by reacting the product of Example O.2. with 10 equivalents of di(isobutyl)aluminium hydride analogously to Example K.3. and working up the reaction product.

Yield: 81% of theory $^1$H NMR (CDCl$_3$): 5.72 (m, 1H, C=CH); 5.50 (m, 1H, C=CH); 3.04–2.77 (m, 6H); 2.60 (m, 1H); 2.49 (s, 3H, N—CH$_3$); 2.31 (bs, 2H, 2xNH); 2.25 (m, 1H); 1.89 ppm (m, 1H).

We claim:

1. A compound of the formula (I)

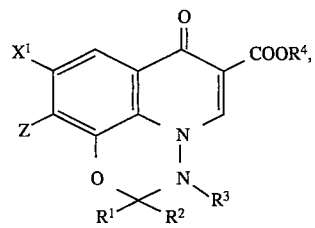

in which $R^1$ is hydrogen or $C_1$–$C_4$-alkyl optionally substituted by hydroxyl or halogen, $R^2$ independently of $R^1$ is hydrogen or methyl, $R^3$ is hydrogen or $C_1$–$C_4$-alkyl, $R^4$ is hydrogen, $C_1$–$C_4$-alkyl optionally substituted by hydroxyl, methoxy, amino, methylamino or dimethylamino, or (5-methyl-2-oxo-1,3-dioxol-4-yl)-methyl, $X^1$ is hydrogen or halogen and Z is a radical of the structure

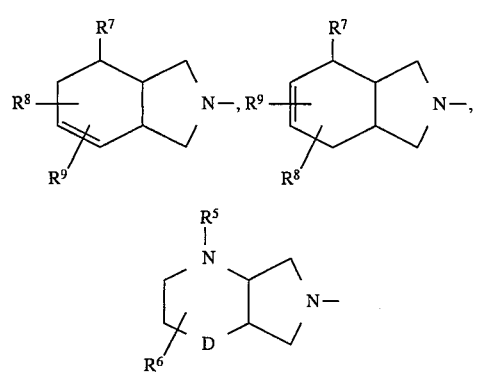

in which $R^7$ is hydrogen, hydroxyl, —$NR^{10}R^{11}$, hydroxymethyl, —$CH_2$—$NR^{10}R^{11}$, carboxyl, methoxycarbonyl or ethoxycarbonyl, $R^{10}$ being hydrogen, $C_1$–$C_3$-alkyl optionally substituted by hydroxyl, alkoxycarbonyl having 1 to 4 C atoms in the alkoxy moiety, or $C_1$–$C_3$-acyl, and $R^{11}$ being hydrogen or methyl, $R^8$ is hydrogen, linear or branched $C_1$–$C_3$-alkyl or cyclopropyl, $R^9$ is hydrogen or methyl, $R^6$ is hydrogen or methyl, $R^5$ is hydrogen, methyl or a radical of the structure
—CH=CH—CO$_2$R$^{5'}$, —CH$_2$—CH$_2$—CO$_2$R$^{5'}$,
—CH$_2$—CO—CH$_3$ or —CH$_2$—CH$_2$—CN, $R^{5'}$ being methyl or ethyl, and D is —CH$_2$—, O or a direct bond, it being possible for the compounds of the formula (I) to be present in the form of racemates or as enantiomerically pure compounds, in the form of their pharmaceutically acceptable hydrates and acid addition salts or in the form of their alkali metal, alkaline earth metal, silver and guanidinium salts.

2. A compound according to claim 1 in which $R^1$ is hydrogen or $C_1$–$C_3$-alkyl optionally substituted by hydroxyl, $R^2$ independently of $R^1$ is hydrogen or methyl, $R^3$ is hydrogen, methyl or ethyl, $R^4$ is hydrogen, $C_1$–$C_4$-alkyl optionally substituted by hydroxyl, methoxy, amino, methylamino or dimethylamino, or (5-methyl-2-oxo-1,3-dioxol-4-yl)methyl, $X^1$ is hydrogen, fluorine or chlorine and Z is a radical of the structure in which $R^7$ is hydrogen, hydroxyl, —NR$^{10}$R$^{11}$, hydroxymethyl or —CH$_2$—NR$^{10}$R$^{11}$, $R^{10}$ being hydrogen, $C_1$–$C_2$-alkyl optionally substituted by hydroxyl, alkoxycarbonyl having 1 to 4 C atoms in the alkoxy moiety, or $C_1$–$C_3$-acyl, and $R^{11}$ being hydrogen or methyl, $R^8$ is hydrogen, linear or branched $C_1$–$C_3$-alkyl or cyclopropyl, $R^9$ is hydrogen or methyl, $R^5$ is hydrogen or methyl, $R^6$ is hydrogen and D is —CH$_2$—, O or a direct bond.

3. A compound of the formula (I) according to claim 1 in which $R^1$ is hydrogen or methyl, $R^2$ is hydrogen, $R^3$ is methyl or ethyl, $R^4$ is hydrogen, methyl or ethyl, $X^1$ is fluorine and Z is a radical of the structure in which $R^7$ is hydrogen, hydroxyl, —NR$^{10}$R$^{11}$, hydroxymethyl or —CH$_2$—NR$^{10}$R$^{11}$, $R^{10}$ being hydrogen, methyl, alkoxycarbonyl having 1 to 4 C atoms in the alkoxy moiety, or $C_1$–$C_3$-acyl, and $R^{11}$ being hydrogen or methyl, $R^8$ is hydrogen, linear or branched $C_1$–$C_3$-alkyl or cyclopropyl, $R^6$ is hydrogen, $R^9$ is hydrogen or methyl, $R^5$ is hydrogen or methyl and D is —CH$_2$—, O or a direct bond.

4. A compound according to claim 1 of the formula or a salt thereof.

5. A compound according to claim 1 of the formula or a salt thereof.

6. A compound according to claim 1, wherein such compound is

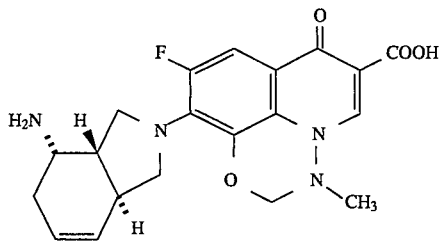

rac.

or a salt thereof.

7. A bactericidal composition comprising a bactericidal effective amount of compound or salt thereof according to claim 1 and a diluent.

8. A method of combatting bacteria in a patient in need thereof which comprises administering to such patient a bactericidally effective amount of compound or salt thereof according to claim 1.

9. The method according to claim 8, wherein the compound is

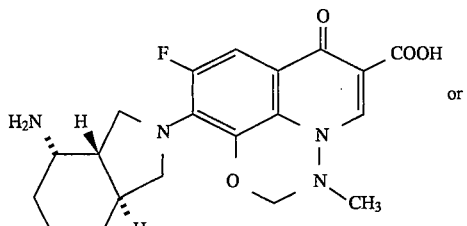

rac.

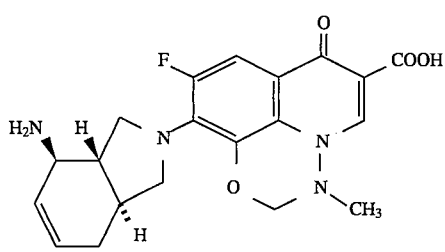

or a salt thereof.

* * * * *

UNITED STATES PATENT AND TRADEMARK OFFICE
CERTIFICATE OF CORRECTION

PATENT NO. : 5,508,278
DATED : April 16, 1996
INVENTOR(S) : Jaetsch, et al.

It is certified that error appears in the above-indentified patent and that said Letters Patent is hereby corrected as shown below:

Col. 57, line 57   Delete " of the formula (I) "

Signed and Sealed this

First Day of October, 1996

Attest:

BRUCE LEHMAN

Attesting Officer    Commissioner of Patents and Trademarks